(12) United States Patent
Doan et al.

(10) Patent No.: US 11,944,816 B2
(45) Date of Patent: Apr. 2, 2024

(54) PARESTHESIA-FREE SPINAL CORD STIMULATION OCCURRING AT LOWER FREQUENCIES AND SWEET SPOT SEARCHING USING PARESTHESIA

(71) Applicant: Boston Scientific Neuromodulation Corporation, Valencia, CA (US)

(72) Inventors: Que T. Doan, West Hills, CA (US); Jianwen Gu, Valencia, CA (US); Ismael Huertas Fernandez, Madrid (ES); Rosana Esteller, Santa Clarita, CA (US); Michael A. Moffitt, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 532 days.

(21) Appl. No.: 17/089,538

(22) Filed: Nov. 4, 2020

(65) Prior Publication Data
US 2021/0046314 A1    Feb. 18, 2021

Related U.S. Application Data

(63) Continuation of application No. 16/806,065, filed on Mar. 2, 2020, now Pat. No. 11,338,141, which is a
(Continued)

(51) Int. Cl.
*A61N 1/36* (2006.01)
*A61N 1/05* (2006.01)
(Continued)

(52) U.S. Cl.
CPC ....... *A61N 1/36062* (2017.08); *A61N 1/0551* (2013.01); *A61N 1/36021* (2013.01);
(Continued)

(58) Field of Classification Search
CPC .. A61N 1/06; A61N 1/36062; A61N 1/36021; A61N 1/36071; A61N 1/36185; A61N 1/37247; A61N 1/0551
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| | (Continued) | |

FOREIGN PATENT DOCUMENTS

| | | |
|---|---|---|
| CN | 202933390 | 5/2013 |
| CN | 102448539 B | 10/2014 |
| | (Continued) | |

OTHER PUBLICATIONS

U.S. Appl. No. 62/860,627, filed Jun. 12, 2019, Esteller et al.
(Continued)

*Primary Examiner* — Joseph M Dietrich
(74) *Attorney, Agent, or Firm* — Lewis & Reese, PLLC

(57) ABSTRACT

Methods and systems for testing and treating spinal cord stimulation (SCS) patients are disclosed. Patients are eventually treated with sub-perception (paresthesia free) therapy. However, supra-perception stimulation is used during "sweet spot searching" during which active electrodes are selected for the patient. This allows sweet spot searching to occur much more quickly and without the need to wash in the various electrode combinations that are tried. After selecting electrodes using supra-perception therapy, therapy is titrated to sub-perception levels using the selected electrodes. Such sub-perception therapy has been investigated using pulses at or below 10 kHz, and it has been determined that a statistically significant correlation exists between pulse width (PW) and frequency (F) in this frequency range at which SCS patients experience significant reduction in symptoms such as back pain. Beneficially, sub-perception
(Continued)

stimulation at such low frequencies significantly lowers power consumption in the patient's neurostimulator.

19 Claims, 18 Drawing Sheets

Related U.S. Application Data continuation of application No. 16/100,904, filed on Aug. 10, 2018, now Pat. No. 10,576,282.

(60) Provisional application No. 62/693,543, filed on Jul. 3, 2018, provisional application No. 62/544,656, filed on Aug. 11, 2017.

(51) Int. Cl.
*A61N 1/372* (2006.01)
*A61N 1/06* (2006.01)

(52) U.S. Cl.
CPC ..... *A61N 1/36071* (2013.01); *A61N 1/36185* (2013.01); *A61N 1/37247* (2013.01); *A61N 1/06* (2013.01); *A61N 1/36132* (2013.01); *A61N 1/37235* (2013.01); *A61N 1/37252* (2013.01)

(56) References Cited

U.S. PATENT DOCUMENTS

| | | | |
|---|---|---|---|
| 7,603,177 B2 | 10/2009 | Sieracki et al. | |
| 8,180,451 B2 | 5/2012 | Hickman et al. | |
| 8,359,102 B2 | 1/2013 | Alataris et al. | |
| 8,515,546 B2 | 8/2013 | Goddard et al. | |
| 8,606,360 B2 | 12/2013 | Butson et al. | |
| 8,606,362 B2 | 12/2013 | He et al. | |
| 8,620,436 B2 | 12/2013 | Parramon et al. | |
| 8,712,533 B2 | 4/2014 | Alataris et al. | |
| 8,792,988 B2 | 7/2014 | Alataris et al. | |
| 9,259,574 B2 | 2/2016 | Aghassian et al. | |
| 9,327,125 B2 | 5/2016 | Alataris et al. | |
| 9,333,357 B2 | 5/2016 | Alataris et al. | |
| 9,446,243 B2 | 9/2016 | Marnfeldt et al. | |
| 9,480,842 B2 | 11/2016 | Alataris et al. | |
| 9,789,252 B2 | 10/2017 | Gerber et al. | |
| 9,792,412 B2 | 10/2017 | Moffitt et al. | |
| 2002/0193833 A1 | 12/2002 | Dimmer et al. | |
| 2009/0204175 A1 | 8/2009 | Zanella et al. | |
| 2010/0023090 A1 | 1/2010 | Jaax et al. | |
| 2010/0274312 A1 | 10/2010 | Alataris et al. | |
| 2010/0305675 A1 | 12/2010 | Laske et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2013/0053923 A1 | 2/2013 | Jaax et al. | |
| 2013/0116752 A1 | 5/2013 | Parker et al. | |
| 2013/0268026 A1 | 10/2013 | Rao et al. | |
| 2014/0277251 A1 | 9/2014 | Gerber et al. | |
| 2014/0277267 A1 | 9/2014 | Vansickle | |
| 2014/0364919 A1 | 12/2014 | Doan | |
| 2015/0080982 A1 | 3/2015 | Funderburk | |
| 2015/0231402 A1 | 8/2015 | Aghassian | |
| 2015/0335893 A1 | 11/2015 | Parker | |
| 2015/0360038 A1 | 12/2015 | Zottola et al. | |
| 2016/0082265 A1 | 3/2016 | Moffitt et al. | |
| 2016/0114166 A1 | 4/2016 | Kaula et al. | |
| 2016/0144183 A1 | 5/2016 | Marnfeldt | |
| 2016/0158551 A1 | 6/2016 | Kent et al. | |
| 2016/0317815 A1 | 11/2016 | Doan et al. | |
| 2016/0361543 A1 | 12/2016 | Kaula et al. | |
| 2016/0367822 A1 | 12/2016 | Parramon | |
| 2017/0050035 A1 | 2/2017 | Gupta et al. | |
| 2017/0056642 A1 | 3/2017 | Moffitt et al. | |
| 2017/0106197 A1 | 4/2017 | Wechter et al. | |
| 2017/0165490 A1 | 6/2017 | Wechter | |
| 2017/0173335 A1 | 6/2017 | Min et al. | |
| 2017/0189685 A1 | 7/2017 | Steinke et al. | |
| 2018/0043172 A1 | 2/2018 | Serrano Carmona | |
| 2018/0071513 A1 | 3/2018 | Weiss et al. | |
| 2018/0071520 A1 | 3/2018 | Weerakoon et al. | |
| 2018/0104493 A1 | 4/2018 | Doan et al. | |
| 2019/0009094 A1 | 1/2019 | Zhang et al. | |
| 2019/0046800 A1 | 2/2019 | Doan et al. | |
| 2019/0083796 A1 | 3/2019 | Weerakoon et al. | |
| 2019/0175915 A1 | 6/2019 | Brill et al. | |
| 2019/0209844 A1 | 7/2019 | Esteller et al. | |
| 2019/0290900 A1 | 9/2019 | Esteller et al. | |
| 2019/0366104 A1 | 12/2019 | Doan et al. | |

FOREIGN PATENT DOCUMENTS

| | | |
|---|---|---|
| EP | 2923727 | 9/2015 |
| JP | 2013-126486 A | 6/2013 |
| WO | 2014/130865 A2 | 8/2014 |
| WO | 2015/066303 A1 | 5/2015 |
| WO | 2016/176425 A1 | 11/2016 |
| WO | 2017/106539 | 6/2017 |

OTHER PUBLICATIONS

L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).
S. Thomson et al., "The PROCO Randomised Controlled Trial: Effects of Pulse Rate on Clinical Outcomes in Kilohertz Frequency Spinal Cord Stimulation—A Multicentre, Double-blind, Crossover Study," presented at the International Neuromodulation Society (INS) Meeting on May 31, 2017.
E.C. Celik et al., "The effect of low-frequency TENS in the treatment of neuropathic pain in patients with spinal cord injury," Spinal Cord 51:34-337 (2013).
Y. Maeda et al., "Low frequencies, but not high frequencies of bi-polar spinal cord stimulation reduce cutaneous and muscle hyperalgesia induced by nerve injury," Pain 138:143-152 (2008).
S. Thomson et al., "Neural Dosing and Energy Requirements in Kilohertz Frequency Spinal Cord Stimulation (SCS)," poster presented at the International Neuromodulation Society (INS) Meeting on May 31, 2017.
S. Paz et al., "Improved Efficacy of SCS Implants Using Multiple Waveforms and Field Shape Options," poster presented at the International Neuromodulation Society (INS) Meeting on May 31, 2017.
S. Paz et al., "Evaluation of Customized Field Shape for Subperception SCS in a Case Series of Chronic Pain Patients," poster presented at the North American Neuromodulation Society (NANS) Meeting on Jan. 11-14, 2018.
S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).
J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).
Yearwood, Thomas, et al., Handout titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood, Thomas, et al., Poster titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 7 pages.

(56) References Cited

OTHER PUBLICATIONS

Yearwood, Thomas, "Neuropathic Extremity Paid and Spinal Cord Stimulation," Pain Medicine, vol. 7, No. S1, 2006, 6 pages.

A. Al-Kaisy et al., "Prospective, Randomized, Sham-Control, Double Blind, Crossover Trial of Subthreshold Spinal Cord Stimulation at Various Kilohertz Frequencies in Subjects Suffering From Failed Back Surgery Syndrome (SCS Frequency Study)," Neuromodulation, vol. 21(5), pp. 457-465 (2018).

M. De Jaeger M et al., "High-Density in Spinal Cord Stimulation: Virtual Expert Registry (Discover): Study Protocol for a Prospective Observational Trial," Anesth. Pain Med., vol. 7(3) (2017).

T.E. Hamm-Faber et al., "High-Dose Spinal Cord Stimulation for Treatment of Chronic Low Back Pain and Leg Pain in Patients With FBSS, 12-Month Results: A Prospective Pilot Study," Neuromodulation, E-pub ahead of print, DOI:10.1111/ner.12940 (2019).

L. Kapural et al., "Novel 10-kHz High-frequency Therapy (HF10 Therapy) Is Superior to Traditional Low-frequency Spinal Cord Stimulation for the Treatment of Chronic Back and Leg Pain: The SENZA-RCT Randomized Controlled Trial," Anesthesiology, vol. 123(4), pp. 851-860 (2015).

J.P. Miller et al., "Parameters of Spinal Cord Stimulation and Their Role in Electrical Charge Delivery: A Review," Neuromodulation, vol. 19(4), pp. 373-384 (2016).

Z. Chen et al., "The Impact of Electrical Charge Delivery on Inhibition of Mechanical Hypersensitivity in Nerve-Injured Rats by Sub-Sensory Threshold Spinal Cord Stimulation," Neuromodulation, vol. 22(2), pp. 163-171 (2019).

F. Yang et al., "Modulation of Spinal Nociceptive Transmission by Sub-Sensory Threshold Spinal Cord Stimulation in Rats After Nerve Injury," Neuromodulation, E-pub ahead of print, DOI:10.1111/ner.12975 (2019).

S.L. Leong et al., "Potential Therapeutic Effect of Low Amplitude Burst Spinal Cord Stimulation on Pain," Neuromodulation, E-pub ahead of print, DOI:10.1111/ner.13090 (2019).

T. Deer et al., "Success Using Neuromodulation With Burst (Sunburst) Study: Results From a Prospective, Randomized Controlled Trial Using a Novel Burst Waveform," Neuromodulation, vol. 21(1), pp. 56-66 (2018).

F. Wille et al., "Altering Conventional to High Density Spinal Cord Stimulation: An Energy Dose-Response Relationship in Neuropathic Pain Therapy," Neuromodulation, vol. 20(1), pp. 71-80 (2017).

J. Vesper et al., "Burst SCS Microdosing Is as Efficacious as Standard Burst SCS in Treating Chronic Back and Leg Pain: Results From a Randomized Controlled Trial," Neuromodulation, vol. 22(2), pp. 190-193 (2019).

E. Tavel et al., "Lower Amplitudes for Burst SCS Programming Associated with Improved Outcomes: Sunburst Sub-Analysis," International Neuromodulation Society (INS) annual meeting, poster, (2017).

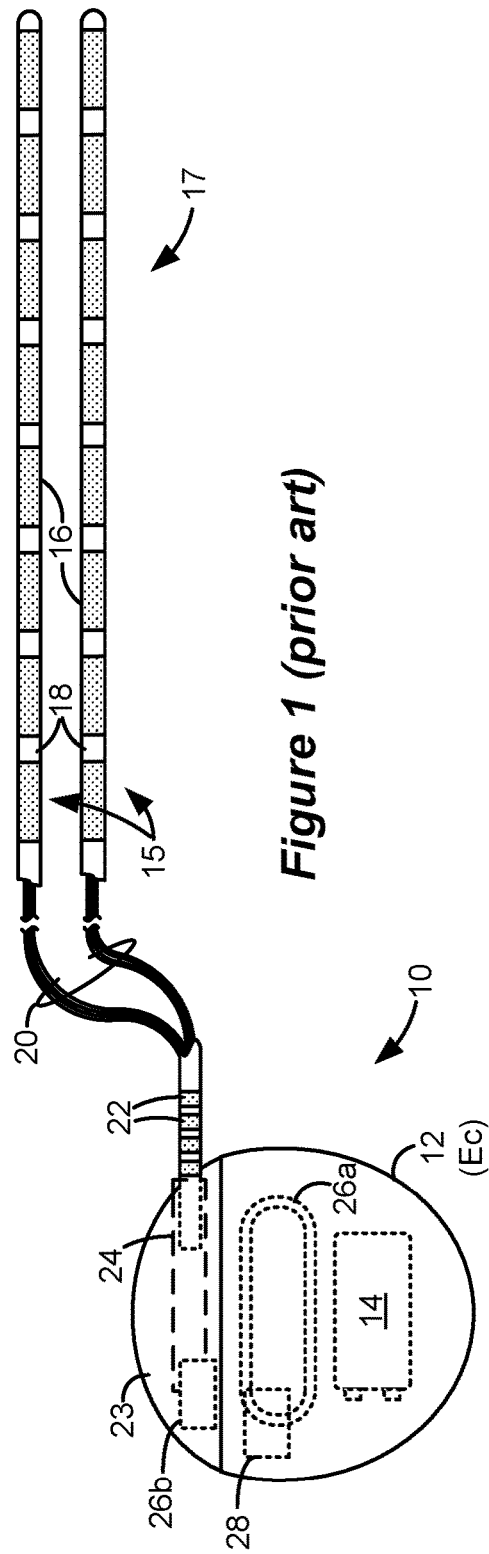
*Figure 1 (prior art)*
*Figure 2 (prior art)*
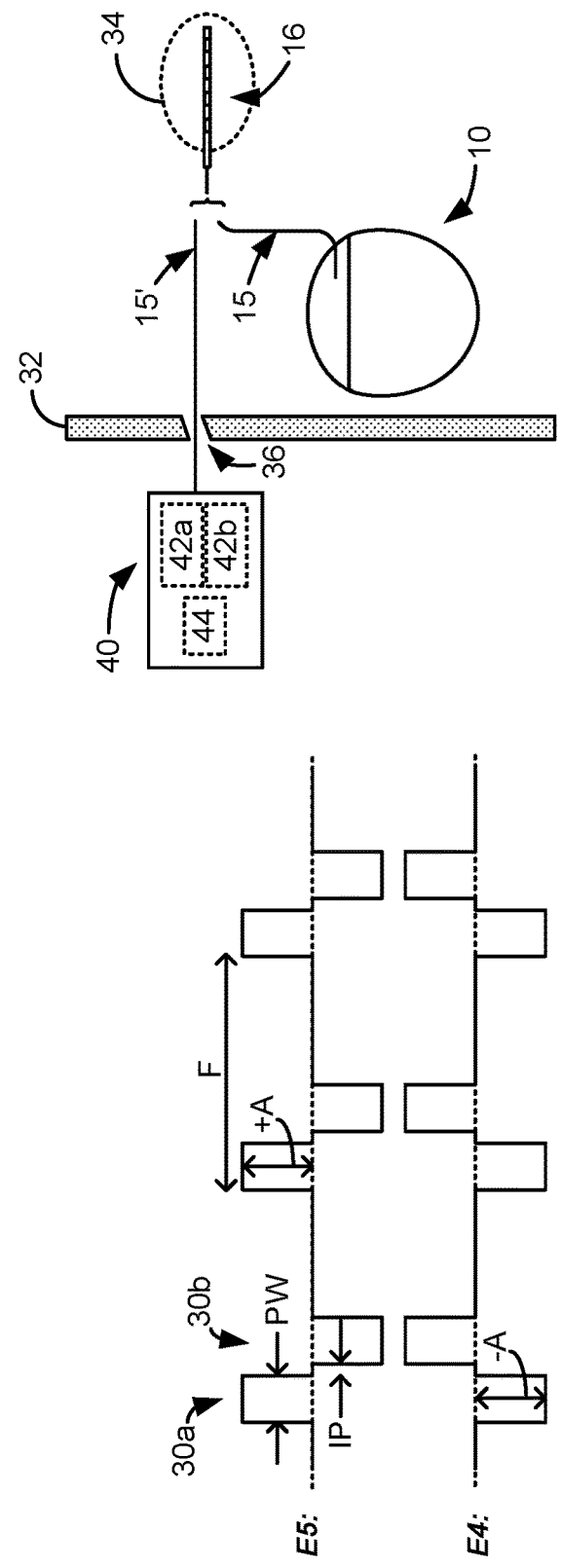
*Figure 3 (prior art)*

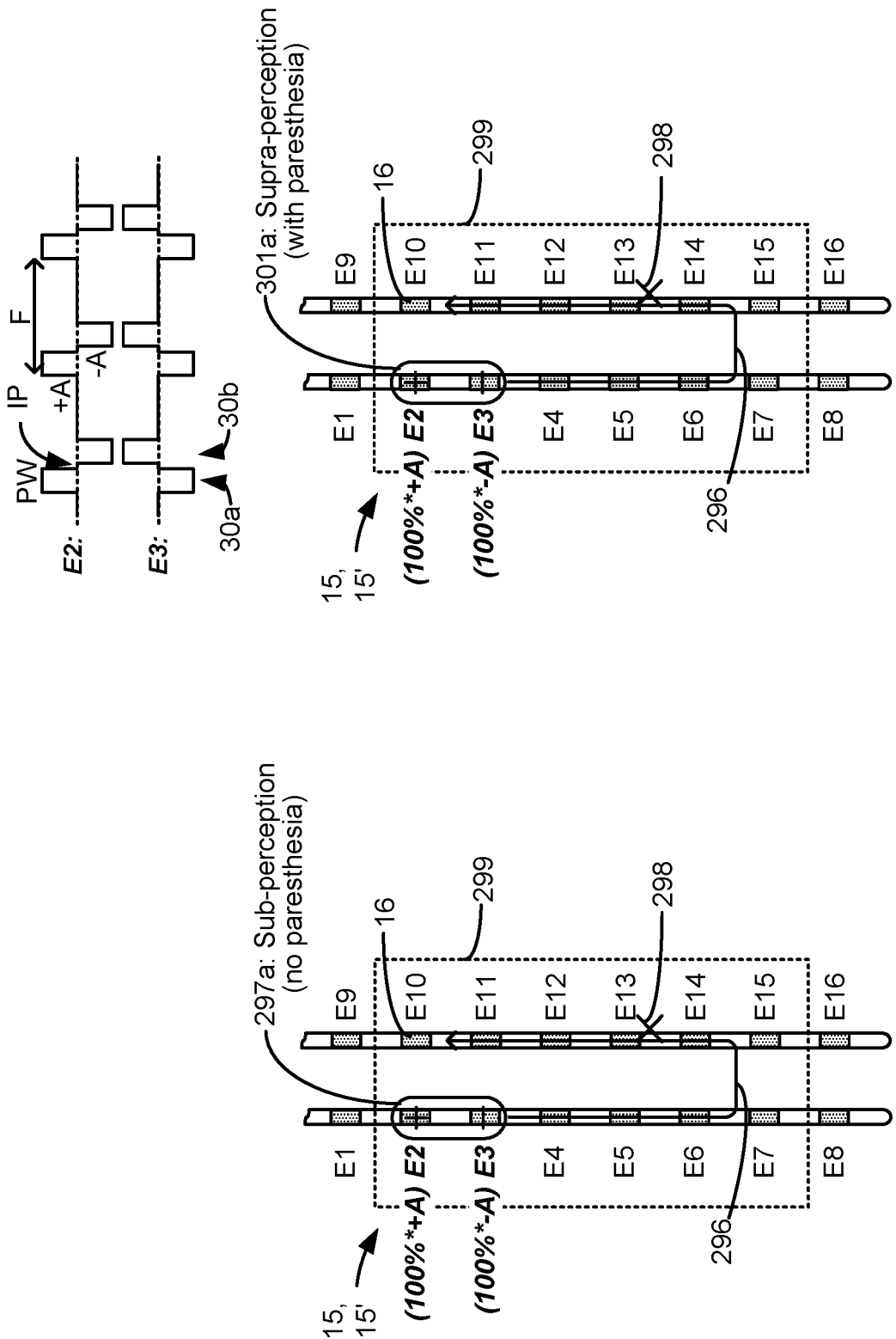

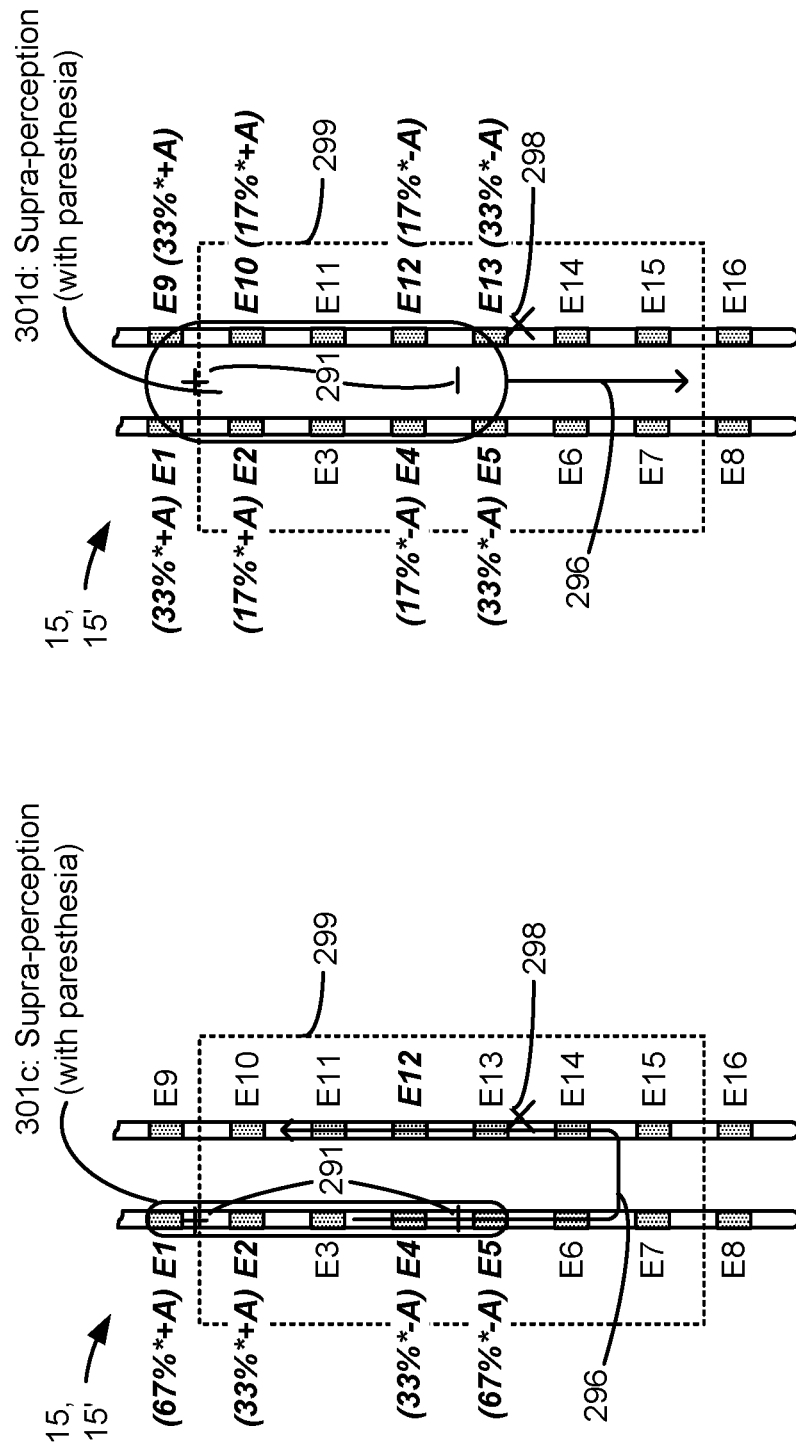

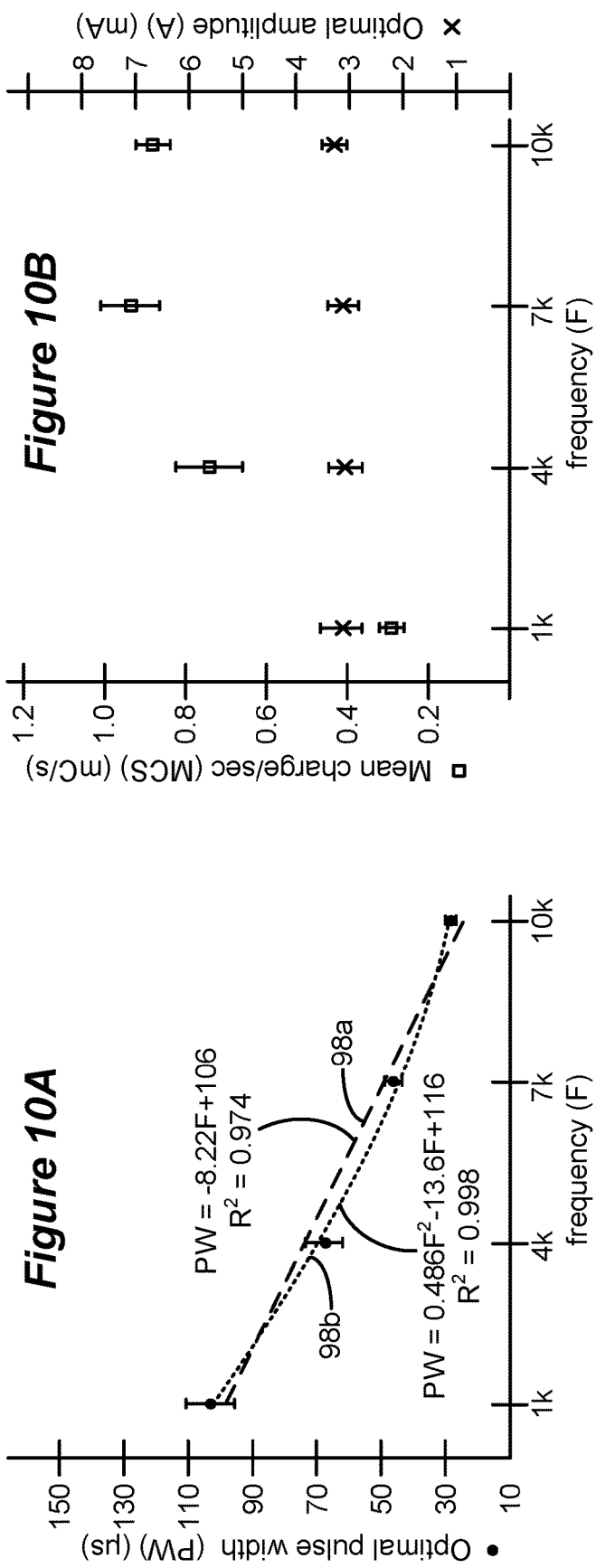
*Figure 10A*
*Figure 10B*
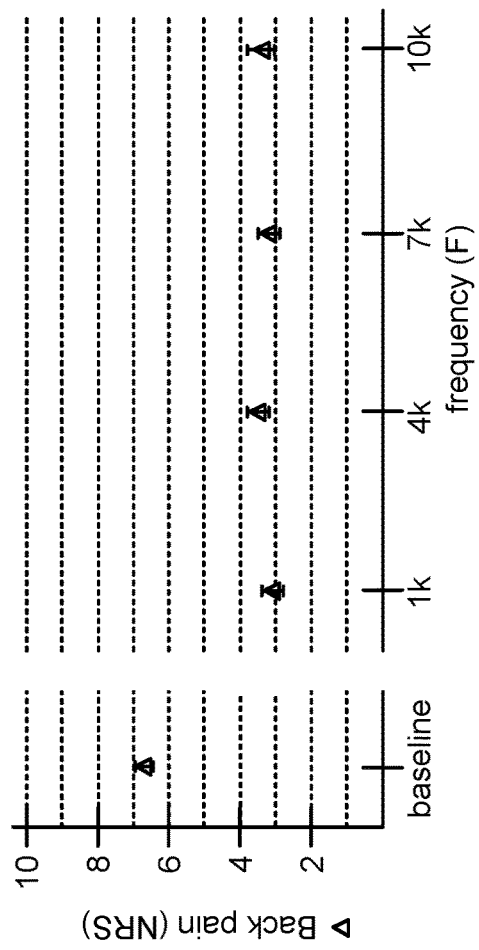
*Figure 10C*

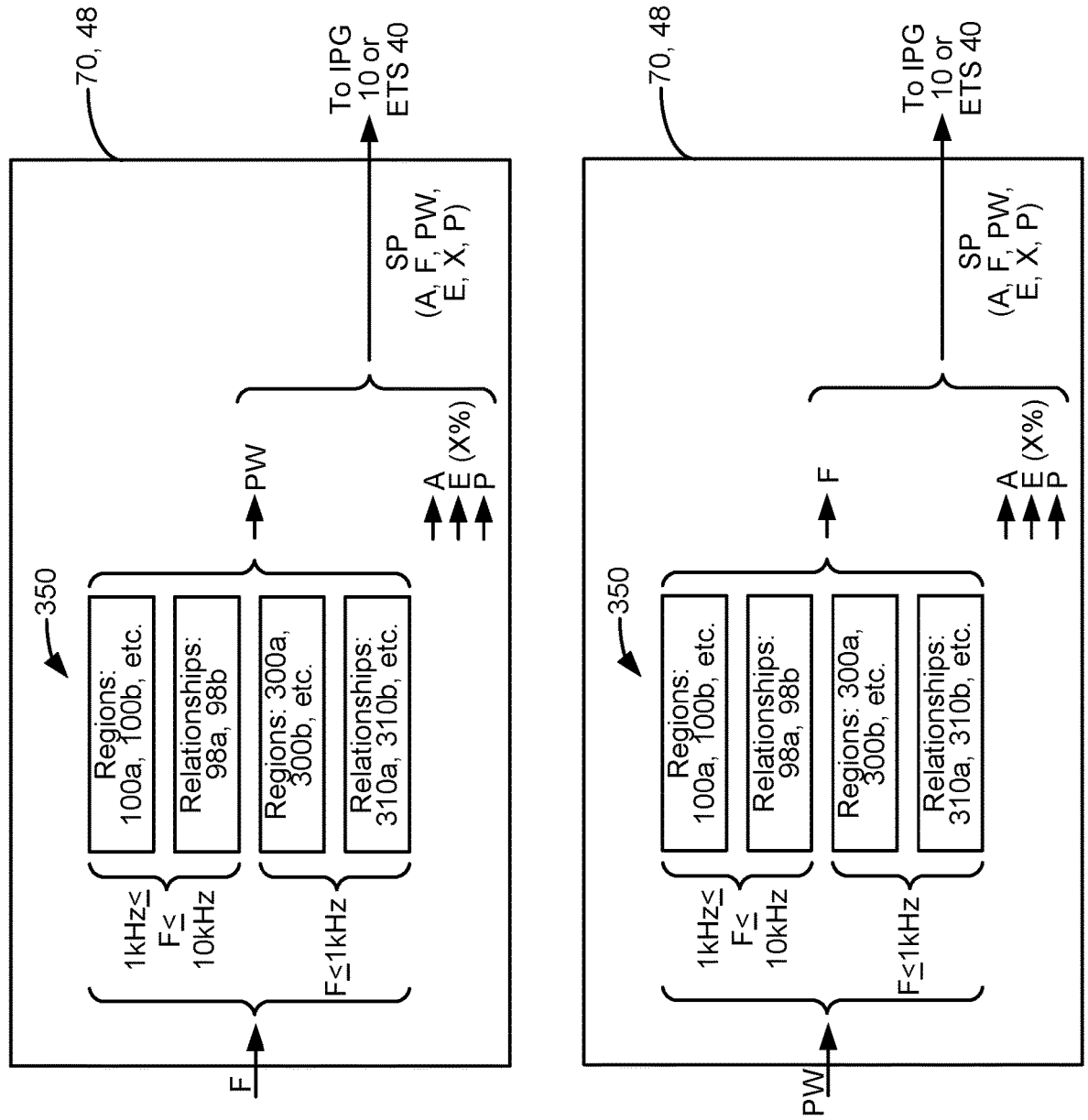

PARESTHESIA-FREE SPINAL CORD STIMULATION OCCURRING AT LOWER FREQUENCIES AND SWEET SPOT SEARCHING USING PARESTHESIA

CROSS-REFERENCE TO RELATED APPLICATIONS

This application is a continuation of U.S. patent application Ser. No. 16/806,065, filed Mar. 2, 2020, which is a continuation of U.S. patent application Ser. No. 16/100,904, filed Aug. 10, 2018 (now U.S. Pat. No. 10,576,282), which is a non-provisional of U.S. Provisional Patent Application Ser. Nos. 62/544,656, filed Aug. 11, 2017, and 62/693,543, filed Jul. 3, 2018. Priority is claimed to these applications, and they are incorporated herein by reference in their entireties.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

In the example of FIG. 2, electrode E5 has been selected as an anode, and thus provides pulses which source a positive current of amplitude +A to the tissue. Electrode E4 has been selected as a cathode, and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripole stimulation, quadripole stimulation, etc.).

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. However, the second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IP) during which no stimulation is provided may be provided between the two phases 30a and 30b.

IPG 10 includes stimulation circuitry 28 that can be programmed to produce the stimulation pulses at the electrodes as defined by the stimulation program. Stimulation circuitry 28 can for example comprise the circuitry described in U.S. Pat. Nos. 10,576,265, 8,606,362 and 8,620,436, and U.S. Patent Application Publication 2018/0071520. These references are incorporated herein by reference.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 such as a microprocessor, microcomputer, an FPGA, other digital logic structures, etc., which is capable of executing instructions an electronic device. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30a. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30a and 30b (e.g., each having a duration of PW, and with opposite polarities +A and −A). An advanced menu 88 can also be used (among other things) to define the relative durations and amplitudes of the pulse phases 30a and 30b, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion.

While GUI 64 is shown as operating in the clinician programmer 50, the user interface of the external controller 45 may provide similar functionality.

SUMMARY

In a first example, a method is disclosed for programming a spinal cord stimulator having a plurality of electrodes comprising an array, which may comprise: programming the spinal cord stimulator implanted in a patient to generate stimulation pulses of a shape comprising a frequency and a pulse width to at least two of a plurality of electrodes, wherein the frequency and the pulse width are selected based on information relating frequencies and pulse widths at which stimulation pulses are formed to provide pain relief to the patient without paresthesia.

The stimulation pulses may form a bipole in the patient's tissue. The spinal cord stimulator may be programmed to generate stimulation pulses to at least three of the plurality of electrodes to form a virtual bipole in the patient's tissue.

The spinal cord stimulator may further comprise control circuitry, wherein the information is stored in the control circuitry. The frequency may be provided to the control circuitry, and the pulse width may be determined using the information. The pulse width may be provided to the control circuitry, and the frequency may be determined using the information. The information may be stored in control circuitry of an external device used to program the spinal cord stimulator. The control circuitry may determine using the information at least one of the frequency or the pulse width at which stimulation pulses are formed to provide pain relief without paresthesia, and the control circuitry may further wirelessly transmit the at least one of the frequency or the pulse width to the spinal cord stimulator. The frequency and pulse width may be selected using the information as a frequency and pulse width that requires a lowest amount of power for the stimulation pulses.

Each of the stimulation pulses may comprise a biphasic pulse having a first phase of a first polarity and a second phase of a second polarity opposite the first polarity, wherein the first and second phases are actively driven by stimulation circuitry in the spinal cord stimulator. Each of the stimulation pulses may comprise a symmetric biphasic pulse, wherein a duration of the first phase is equal to a duration of the second phase, and wherein an amplitude of the first phase is equal but of opposite polarity to an amplitude of the second phase. The pulse width may comprise (i) a total duration of the first and second phases, or (ii) a duration of either the first phase or the second phase.

The frequency may be 1 kHz, or lower than 1 kHz. The frequency and pulse width at which stimulation pulses are formed to provide pain relief without paresthesia may be on or within a linearly-bounded region defined by points (10 Hz, 265 µs), (10 Hz, 435 µs), (50 Hz, 370 µs), and (50 Hz, 230 µs), (50 Hz, 230 µs), (50 Hz, 370 µs), (100 Hz, 325 µs), and (100 Hz, 195 µs), (100 Hz, 195 µs), (100 Hz, 325 µs), (200 Hz, 260 µs), and (200 Hz, 160 µs), (200 Hz, 160 µs), (200 Hz, 260 µs), (400 Hz, 225 µs), and (400 Hz, 140 µs), (400 Hz, 140 µs), (400 Hz, 225 µs), (600 Hz, 200 µs), and (600 Hz, 120 µs), (600 Hz, 120 µs), (600 Hz, 200 µs), (800 Hz, 175 µs), and (800 Hz, 105 µs), or (800 Hz, 105 µs), (800 Hz, 175 µs), (1000 Hz, 150 µs), and (1000 Hz, 90 µs).

The frequency and pulse width at which stimulation pulses are formed to provide pain relief without paresthesia may not comprise a duty cycle relating frequency and pulse width that is constant lower than 1 kHz.

The frequency may be in a range of 1 kHz to 10 kHz. The frequency and pulse width at which stimulation pulses are formed to provide pain relief without paresthesia may be on or within one or more linearly-bounded regions defined by points:

(i) (1 kHz, 98.3 µs), (1 kHz, 109 µs), (4 kHz, 71.4 µs), and (4 kHz, 64.6 µs); or (ii) (4 kHz, 71.4 µs), (4 kHz, 64.6 µs), (7 kHz, 44.2 µs), and (7 kHz, 48.8 µs); or (iii) (7 kHz, 44.2 µs), (7 kHz, 48.8 µs), (10 kHz, 29.9 µs), and (10 kHz, 27.1 µs). or (i) (1 kHz, 96.3 µs), (1 kHz, 112 µs), (4 kHz, 73.8 µs), and (4 kHz, 62.2 µs); or (ii) (4 kHz, 73.8 µs), (4 kHz, 62.2 µs), (7 kHz, 43.6 µs), and (7 kHz, 49.4 µs); or (iii) (7 kHz, 43.6 µs), (7 kHz, 49.4 µs), (10 kHz, 30.0 µs), and (10 kHz, 27.0 µs).

or (i) (1 kHz, 69.6 µs), (1 kHz, 138.4 µs), (4 kHz, 93.9 µs), and (4 kHz, 42.1 µs); or (ii) (4 kHz, 93.9 µs), (4 kHz, 42.1 µs), (7 kHz, 33.4 µs), and (7 kHz, 59.6 µs); or (iii) (7 kHz, 33.4 µs), (7 kHz, 59.6 µs), (10 kHz, 35.2 µs), and (10 kHz, 21.8 µs).

or (i) (1 kHz, 50.0 µs), (1 kHz, 200.0 µs), (4 kHz, 110.0 µs), and (4 kHz, 30.0 µs); or (ii) (4 kHz, 110.0 µs), (4 kHz, 30.0 µs), (7 kHz, 30.0 µs), and (7 kHz, 60.0 µs); or (iii) (7 kHz, 30.0 µs), (7 kHz, 60.0 µs), (10 kHz, 40.0 µs), and (10 kHz, 20.0 µs).

The method may further comprise steering current between the plurality of electrodes to adjust a location at which the stimulation pulses are applied to the patient. The method may further comprise adjusting an amplitude of the stimulation pulses based on the adjusted location at which the stimulation pulses are applied to the patient.

The frequency, pulse width, and amplitude may comprise three of a set of stimulation parameters used to generate the stimulation pulses, and the method may further comprise reducing at least one of the stimulation parameters to or by a set amount or percentage in response to an instruction. The stimulation circuitry in response to the instruction may reduce the amplitude of the stimulation pulses to or by a set amount or percentage.

The frequency and pulse width may comprise two of a set of stimulation parameters used to generate the stimulation pulses, and the method may further comprise adjusting at least one of the stimulation parameters in response to a change in position or activity of the patient. The spinal cord stimulator may be programmed during a programming session, and the stimulation pulses may be washed in for a period of one hour or less during the programming session to provide pain relief to the patient without paresthesia.

In a second example, a system is disclosed, which may comprise: a spinal cord stimulator, comprising stimulation circuitry programmed to generate stimulation pulses of a shape comprising a frequency and a pulse width to at least one of a plurality of electrodes, wherein the frequency and the pulse width are selected based on information relating frequencies and pulse widths at which stimulation pulses are formed to provide pain relief without paresthesia.

The stimulation pulses may be configured to form a bipole in the patient's tissue. The stimulation circuitry may be programmed to generate stimulation pulses to at least three of the plurality of electrodes to form a virtual bipole in the patient's tissue. The spinal cord stimulator may further comprise control circuitry, wherein the information is stored in the control circuitry. The frequency may be provided to the control circuitry, and the pulse width may be determined using the information. The pulse width may be provided to the control circuitry, and the frequency may be determined using the information.

The system may further comprise an external device comprising control circuitry, wherein the information is stored in the control circuitry. The control circuitry may be configured to determine using the information at least one of the frequency or the pulse width at which stimulation pulses are formed to provide pain relief without paresthesia, and wherein the control circuitry is further configured to wirelessly transmit the at least one of the frequency or the pulse width to the spinal cord stimulator.

The frequency and pulse width may be selected using the information as a frequency and pulse width that requires a lowest amount of power for the stimulation pulses.

Each of the stimulation pulses may comprise a biphasic pulse having a first phase of a first polarity and a second phase of a second polarity opposite the first polarity, wherein the first and second phases are actively driven by stimulation circuitry in the spinal cord stimulator. Each of the stimulation pulses may comprise a symmetric biphasic pulse, wherein a duration of the first phase is equal to a duration of the second phase, and wherein an amplitude of the first phase is equal but of opposite polarity to an amplitude of the second phase. The pulse width may comprise (i) a total duration of the first and second phases, or (ii) a duration of either the first phase or the second phase.

The frequency may be 1 kHz or lower than 1 kHz. The frequency and pulse width at which stimulation pulses are formed to provide pain relief without paresthesia are on or within a linearly-bounded region defined by points (10 Hz, 265 µs), (10 Hz, 435 µs), (50 Hz, 370 µs), and (50 Hz, 230 µs), (50 Hz, 230 µs), (50 Hz, 370 µs), (100 Hz, 325 µs), and (100 Hz, 195 µs), (100 Hz, 195 µs), (100 Hz, 325 µs), (200 Hz, 260 µs), and (200 Hz, 160 µs), (200 Hz, 160 µs), (200 Hz, 260 µs), (400 Hz, 225 µs), and (400 Hz, 140 µs), (400 Hz, 140 µs), (400 Hz, 225 µs), (600 Hz, 200 µs), and (600 Hz, 120 µs), (600 Hz, 120 µs), (600 Hz, 200 µs), (800 Hz, 175 µs), and (800 Hz, 105 µs), or (800 Hz, 105 µs), (800 Hz, 175 µs), (1000 Hz, 150 µs), and (1000 Hz, 90 µs).

The frequency and pulse width at which stimulation pulses are formed to provide pain relief without paresthesia may not comprise a duty cycle relating frequency and pulse width that is constant in a range of 10 Hz through 1 kHz.

The frequency may be in a range of 1 kHz to 10 kHz. The frequency and pulse width at which stimulation pulses are formed to provide pain relief without paresthesia may be on or within one or more linearly-bounded regions defined by points:

(i) (1 kHz, 98.3 µs), (1 kHz, 109 µs), (4 kHz, 71.4 µs), and (4 kHz, 64.6 µs); or (ii) (4 kHz, 71.4 μs), (4 kHz, 64.6 μs), (7 kHz, 44.2 μs), and (7 kHz, 48.8 μs); or
(iii) (7 kHz, 44.2 μs), (7 kHz, 48.8 μs), (10 kHz, 29.9 μs), and (10 kHz, 27.1 μs).
or
(i) (1 kHz, 96.3 μs), (1 kHz, 112 μs), (4 kHz, 73.8 μs), and (4 kHz, 62.2 μs); or
(ii) (4 kHz, 73.8 μs), (4 kHz, 62.2 μs), (7 kHz, 43.6 μs), and (7 kHz, 49.4 μs); or
(iii) (7 kHz, 43.6 μs), (7 kHz, 49.4 μs), (10 kHz, 30.0 μs), and (10 kHz, 27.0 μs).
or
(i) (1 kHz, 69.6 μs), (1 kHz, 138.4 μs), (4 kHz, 93.9 μs), and (4 kHz, 42.1 μs); or
(ii) (4 kHz, 93.9 μs), (4 kHz, 42.1 μs), (7 kHz, 33.4 μs), and (7 kHz, 59.6 μs); or
(iii) (7 kHz, 33.4 μs), (7 kHz, 59.6 μs), (10 kHz, 35.2 μs), and (10 kHz, 21.8 μs).
or
(i) (1 kHz, 50.0 μs), (1 kHz, 200.0 μs), (4 kHz, 110.0 μs), and (4 kHz, 30.0 μs); or
(ii) (4 kHz, 110.0 μs), (4 kHz, 30.0 μs), (7 kHz, 30.0 μs), and (7 kHz, 60.0 μs); or
(iii) (7 kHz, 30.0 μs), (7 kHz, 60.0 μs), (10 kHz, 40.0 μs), and (10 kHz, 20.0 μs).

The stimulation circuitry may be configurable to steer current between the plurality of electrodes to adjust a location at which the stimulation pulses are applied to the patient. The stimulation circuitry may be further configured to adjust an amplitude of the stimulation pulses based on the adjusted location at which the stimulation pulses are applied to the patient.

The frequency, pulse width, and amplitude may comprise three of a set of stimulation parameters used to generate the stimulation pulses, wherein the stimulation circuitry is configurable in response to an instruction to reduce at least one of the stimulation parameters to or by a set amount or percentage.

The frequency and pulse width may comprise two of a set of stimulation parameters used to generate the stimulation pulses, and wherein the stimulation circuitry is configurable to adjust at least one of the stimulation parameters in response to a change in position or activity of the patient.

The spinal cord stimulator may be configured to be programmable during a programming session, and wherein the spinal cord stimulator is configured to wash in the stimulation pulses for a period of one hour or less during the programming session to provide pain relief to the patient without paresthesia.

In a third example, a method is disclosed for programming a spinal cord stimulator having a plurality of electrodes comprising an array, which may comprise: (a) providing to the spinal cord stimulator a plurality of different sets of first stimulation parameters, wherein each first stimulation parameters set causes the spinal cord stimulator to form biphasic test pulses at at least two of the electrodes, wherein each biphasic test pulse comprises a first phase of a first polarity and a second phase of a second polarity opposite the first polarity, wherein the first and second pulse phases are both actively driven by stimulation circuitry in the spinal cord stimulator, and wherein each first stimulation parameters set causes supra-perception stimulation to occur at different locations relative to the array; (b) determining a set of the first stimulation parameters that treats a pain symptom of the patient, the determined first stimulation parameters set corresponding to a therapy location relative to the array; and (c) providing to the spinal cord stimulator a set of second stimulation parameters to cause the spinal cord stimulator to form therapeutic pulses at at least two of the electrodes, wherein the second stimulation parameters set causes sub-perception stimulation to occur at the therapy location.

The biphasic test pulses may be formed at 130 Hz or less. A charge of the first phase may equal a charge of the second phase. A duration of the first phase may be different from a duration of the second phase, and an amplitude of the first phase may be different from an amplitude of the second phase. The biphasic test pulses may comprise symmetric biphasic pulses, wherein a duration of the first phase is equal to a duration of the second phase, and wherein an amplitude of the first phase is equal to but of opposite polarity to an amplitude of the second phase. A charge of the first phase may not equal a charge of the second phase.

The therapeutic pulses may comprise biphasic pulses having a first phase of a first polarity and a second phase of a second polarity opposite the first polarity. The therapeutic pulses may comprise symmetric biphasic pulses, wherein a duration of the first phase is equal to a duration of the second phase, and wherein an amplitude of the first phase is equal but of opposite polarity to an amplitude of the second phase.

The second stimulation parameters set may determined by adjusting at least one of the stimulation parameters of the determined first stimulation parameters set without adjusting the therapy location relative to the array. The determined first stimulation parameters set may comprise a set of stimulation parameters to which the patient responds favorably to treatment of the pain symptom.

Each first stimulation parameters set may cause supra-perception stimulation to occur as a multipole at the different locations. At least some or all of the first stimulation parameters sets may cause supra-perception to occur as a bipole at the different locations. At least some of the first stimulation parameters sets may cause supra-perception stimulation to occur as a virtual bipole at the different locations. The second stimulation parameters may cause sub-perception stimulation to occur as a multipole at the therapy location. The second stimulation parameters may cause sub-perception stimulation to occur as a bipole at the therapy location. The second stimulation parameters may cause sub-perception stimulation to occur as a virtual bipole at the therapy location.

The determined first stimulation parameters set may be determined using feedback from the patient. The determined first stimulation parameters set may comprise an amplitude of the test pulses, and wherein the set of second stimulation parameters comprises an amplitude of the therapeutic pulses, and wherein the amplitude of the therapeutic pulses is lower than the amplitude of the test pulses. The determined first stimulation parameters set may differ from the second stimulation parameters set only in the amplitudes of the test and therapeutic pulses.

Each first stimulation parameters set and the second stimulation parameters set may comprise an indication of which of the at least two electrodes are active, an indication of the polarity of the at least two electrodes, and an indication of an amplitude of a current at the at least two electrodes.

The second stimulation parameters set may comprise a frequency and pulse width of the therapeutic pulses, wherein the frequency is 10 kHz or lower, and wherein at least one of the frequency and the pulse width are selected to cause the sub-perception stimulation to occur. The selected frequency and pulse width may be on or within one or more linearly-bounded regions defined by points:

(i) (10 Hz, 265 µs), (10 Hz, 435 µs), (50 Hz, 370 µs), and (50 Hz, 230 µs); or
(ii) (50 Hz, 230 µs), (50 Hz, 370 µs), (100 Hz, 325 µs), and (100 Hz, 195 µs); or
(iii) (100 Hz, 195 µs), (100 Hz, 325 µs), (200 Hz, 260 µs), and (200 Hz, 160 µs); or
(iv) (200 Hz, 160 µs), (200 Hz, 260 µs), (400 Hz, 225 µs), and (400 Hz, 140 µs); or
(v) (400 Hz, 140 µs), (400 Hz, 225 µs), (600 Hz, 200 µs), and (600 Hz, 120 µs); or
(vi) (600 Hz, 120 µs), (600 Hz, 200 µs), (800 Hz, 175 µs), and (800 Hz, 105 µs); or
(vii) (800 Hz, 105 µs), (800 Hz, 175 µs), (1000 Hz, 150 µs), and (1000 Hz, 90 µs).

The selected frequency and pulse width may be on or within one or more linearly-bounded regions defined by points:
(i) (1 kHz, 98.3 µs), (1 kHz, 109 µs), (4 kHz, 71.4 µs), and (4 kHz, 64.6 µs); or
(ii) (4 kHz, 71.4 µs), (4 kHz, 64.6 µs), (7 kHz, 44.2 µs), and (7 kHz, 48.8 µs); or
(iii) (7 kHz, 44.2 µs), (7 kHz, 48.8 µs), (10 kHz, 29.9 µs), and (10 kHz, 27.1 µs).
or
(i) (1 kHz, 96.3 µs), (1 kHz, 112 µs), (4 kHz, 73.8 µs), and (4 kHz, 62.2 µs); or
(ii) (4 kHz, 73.8 µs), (4 kHz, 62.2 µs), (7 kHz, 43.6 µs), and (7 kHz, 49.4 µs); or
(iii) (7 kHz, 43.6 µs), (7 kHz, 49.4 µs), (10 kHz, 30.0 µs), and (10 kHz, 27.0 µs).
or
(i) (1 kHz, 69.6 µs), (1 kHz, 138.4 µs), (4 kHz, 93.9 µs), and (4 kHz, 42.1 µs); or
(ii) (4 kHz, 93.9 µs), (4 kHz, 42.1 µs), (7 kHz, 33.4 µs), and (7 kHz, 59.6 µs); or
(iii) (7 kHz, 33.4 µs), (7 kHz, 59.6 µs), (10 kHz, 35.2 µs), and (10 kHz, 21.8 µs).
or
(i) (1 kHz, 50.0 µs), (1 kHz, 200.0 µs), (4 kHz, 110.0 µs), and (4 kHz, 30.0 µs); or
(ii) (4 kHz, 110.0 µs), (4 kHz, 30.0 µs), (7 kHz, 30.0 µs), and (7 kHz, 60.0 µs); or
(iii) (7 kHz, 30.0 µs), (7 kHz, 60.0 µs), (10 kHz, 40.0 µs), and (10 kHz, 20.0 µs).

The frequency and the pulse width may be selected based on information relating frequencies and pulse widths at which the therapeutic pulses are formed to cause sub-perception stimulation to occur at the therapy location. The first and second stimulation parameters set may be provided to the spinal cord stimulator by an external device, and wherein the information is stored on the external device. The information may be stored in the spinal cord stimulator. The frequency and pulse width may be selected using the information as a frequency and pulse width that requires a lowest amount of power for the therapeutic pulses.

The method may further comprise steering current between the plurality of electrodes to adjust the therapy location to a new therapy location relative to the array. The method may further comprise adjusting an amplitude of the therapeutic pulses based on the new therapy location.

The determined first stimulation parameters set may comprises an first amplitude of the test pulses, and the method may further comprise, in response to an instruction, deriving the second stimulation parameters set from the determined first stimulation parameter set by reducing the first amplitude to a second amplitude for the therapeutic pulses. The first amplitude may be reduced to the second amplitude to or by a set amount or percentage.

The method may further comprise adjusting at least one of the stimulation parameters of the second stimulation parameters set in response to a change in position or activity of the patient. The spinal cord stimulator may programmed during a programming session, and the therapeutic pulses may be washed in for a period of one hour or less during the programming session to causes sub-perception stimulation to occur at the therapy location.

In a fourth example, a system is for programming a spinal cord stimulator having a plurality of electrodes comprising an array, which may comprise: an external system a non-transitory computer readable media containing instructions that when executed allows the external device to provide to the spinal cord stimulator a plurality of different sets of first stimulation parameters, wherein each first stimulation parameters set causes the spinal cord stimulator to form biphasic test pulses at at least two of the electrodes, wherein each biphasic test pulse comprises a first phase of a first polarity and a second phase of a second polarity opposite the first polarity, wherein the first and second pulse phases are both actively driven by stimulation circuitry in the spinal cord stimulator, and wherein each first stimulation parameters set causes supra-perception stimulation to occur at different locations relative to the array; wherein after determining a set of the first stimulation parameters that treats a pain symptom of the patient, the determined first stimulation parameters set corresponding to a therapy location relative to the array, the instructions when executed further allow the external device to provide to the spinal cord stimulator a set of second stimulation parameters to cause the spinal cord stimulator to form therapeutic pulses at at least two of the electrodes, wherein the second stimulation parameters set causes sub-perception stimulation to occur at the therapy location.

The biphasic test pulses may be formed at 130 Hz or less. A charge of the first phase may equal a charge of the second phase. A duration of the first phase may be different from a duration of the second phase, and an amplitude of the first phase may be different from an amplitude of the second phase. The biphasic test pulses may comprise symmetric biphasic pulses, wherein a duration of the first phase is equal to a duration of the second phase, and wherein an amplitude of the first phase is equal to but of opposite polarity to an amplitude of the second phase. A charge of the first phase may not equal a charge of the second phase.

The therapeutic pulses may comprise biphasic pulses having a first phase of a first polarity and a second phase of a second polarity opposite the first polarity. The therapeutic pulses may comprise symmetric biphasic pulses, wherein a duration of the first phase is equal to a duration of the second phase, and wherein an amplitude of the first phase is equal but of opposite polarity to an amplitude of the second phase.

The non-transitory computer readable media may be configured to determine the second stimulation parameters set by adjusting at least one of the stimulation parameters of the determined first stimulation parameters set without adjusting the therapy location relative to the array. The determined first stimulation parameters set may comprise a set of stimulation parameters to which the patient responds favorably to treatment of the pain symptom.

Each first stimulation parameters set may cause supra-perception stimulation to occur as a multipole at the different locations. At least some or all of the first stimulation parameters sets may cause supra-perception to occur as a bipole at the different locations. At least some of the first stimulation parameters sets may cause supra-perception stimulation to occur as a virtual bipole at the different locations. The second stimulation parameters may cause sub-perception stimulation to occur as a multipole at the therapy location. The second stimulation parameters may cause sub-perception stimulation to occur as a bipole at the therapy location. The second stimulation parameters may cause sub-perception stimulation to occur as a virtual bipole at the therapy location.

The determined first stimulation parameters set may be determined using feedback from the patient. The determined first stimulation parameters set may comprise an amplitude of the test pulses, and wherein the set of second stimulation parameters comprises an amplitude of the therapeutic pulses, and wherein the amplitude of the therapeutic pulses is lower than the amplitude of the test pulses. The determined first stimulation parameters set may differ from the second stimulation parameters set only in the amplitudes of the test and therapeutic pulses.

Each first stimulation parameters set and the second stimulation parameters set may comprise an indication of which of the at least two electrodes are active, an indication of the polarity of the at least two electrodes, and an indication of an amplitude of a current at the at least two electrodes.

The second stimulation parameters set may comprise a frequency and pulse width of the therapeutic pulses, wherein the frequency is 10 kHz or lower, and wherein at least one of the frequency and the pulse width are selected by the computer readable media to cause the sub-perception stimulation to occur. The selected frequency and pulse width may be on or within one or more linearly-bounded regions defined by points:
- (i) (10 Hz, 265 μs), (10 Hz, 435 μs), (50 Hz, 370 μs), and (50 Hz, 230 μs); or
- (ii) (50 Hz, 230 μs), (50 Hz, 370 μs), (100 Hz, 325 μs), and (100 Hz, 195 μs); or
- (iii) (100 Hz, 195 μs), (100 Hz, 325 μs), (200 Hz, 260 μs), and (200 Hz, 160 μs); or
- (iv) (200 Hz, 160 μs), (200 Hz, 260 μs), (400 Hz, 225 μs), and (400 Hz, 140 μs); or
- (v) (400 Hz, 140 μs), (400 Hz, 225 μs), (600 Hz, 200 μs), and (600 Hz, 120 μs); or
- (vi) (600 Hz, 120 μs), (600 Hz, 200 μs), (800 Hz, 175 μs), and (800 Hz, 105 μs); or
- (vii) (800 Hz, 105 μs), (800 Hz, 175 μs), (1000 Hz, 150 μs), and (1000 Hz, 90 μs).

The selected frequency and pulse width may be on or within one or more linearly-bounded regions defined by points:
- (i) (1 kHz, 98.3 μs), (1 kHz, 109 μs), (4 kHz, 71.4 μs), and (4 kHz, 64.6 μs); or
- (ii) (4 kHz, 71.4 μs), (4 kHz, 64.6 μs), (7 kHz, 44.2 μs), and (7 kHz, 48.8 μs); or
- (iii) (7 kHz, 44.2 μs), (7 kHz, 48.8 μs), (10 kHz, 29.9 μs), and (10 kHz, 27.1 μs).

or
- (i) (1 kHz, 96.3 μs), (1 kHz, 112 μs), (4 kHz, 73.8 μs), and (4 kHz, 62.2 μs); or
- (ii) (4 kHz, 73.8 μs), (4 kHz, 62.2 μs), (7 kHz, 43.6 μs), and (7 kHz, 49.4 μs); or
- (iii) (7 kHz, 43.6 μs), (7 kHz, 49.4 μs), (10 kHz, 30.0 μs), and (10 kHz, 27.0 μs).

or
- (i) (1 kHz, 69.6 μs), (1 kHz, 138.4 μs), (4 kHz, 93.9 μs), and (4 kHz, 42.1 μs); or
- (ii) (4 kHz, 93.9 μs), (4 kHz, 42.1 μs), (7 kHz, 33.4 μs), and (7 kHz, 59.6 μs); or
- (iii) (7 kHz, 33.4 μs), (7 kHz, 59.6 μs), (10 kHz, 35.2 μs), and (10 kHz, 21.8 μs).

or
- (i) (1 kHz, 50.0 μs), (1 kHz, 200.0 μs), (4 kHz, 110.0 μs), and (4 kHz, 30.0 μs); or
- (ii) (4 kHz, 110.0 μs), (4 kHz, 30.0 μs), (7 kHz, 30.0 μs), and (7 kHz, 60.0 μs); or
- (iii) (7 kHz, 30.0 μs), (7 kHz, 60.0 μs), (10 kHz, 40.0 μs), and (10 kHz, 20.0 μs).

The frequency and the pulse width may be selected by the computer readable media based on information relating frequencies and pulse widths at which the therapeutic pulses are formed to cause sub-perception stimulation to occur at the therapy location. The frequency and pulse width may be selected using the information as a frequency and pulse width that requires a lowest amount of power for the therapeutic pulses.

The computer readable media may contains instructions that when executed allow the external device to steer current between the plurality of electrodes to adjust the therapy location to a new therapy location relative to the array. The computer readable media may further contains instructions that when executed allow the external device to adjust an amplitude of the therapeutic pulses based on the new therapy location. The computer readable media may further contain instructions that when executed allow the external device to reduce at least one of the stimulation parameters of the second stimulation parameters set to or by a set amount or percentage.

The computer readable media may further contain instructions that when executed allow the external device to adjust at least one of the stimulation parameters of the second stimulation parameters set in response to a change in position or activity of the patient. The computer readable media may further contain instructions that when executed allow the external device to program the spinal cord stimulator during a programming session, and wherein the instructions are configured to wash in the therapeutic pulses for a period of one hour or less during the programming session to causes sub-perception stimulation to occur at the therapy location.

BRIEF DESCRIPTION OF THE DRAWINGS

FIG. 1 shows an Implantable Pulse Generator (IPG) useable for Spinal Cord Stimulation (SCS), in accordance with the prior art.

FIG. 2 shows an example of stimulation pulses producible by the IPG, in accordance with the prior art.

FIG. 3 shows use of an External Trial Stimulator (ETS) useable to provide stimulation before implantation of an IPG, in accordance with the prior art.

FIG. 6 shows sweet spot searching to determine effective electrodes for a patient using a movable sub-perception bipole.

FIGS. 7A-7D show sweet spot searching to determine effective electrodes for a patient using a movable supra-perception bipole.

FIGS. 10A-10C show various results of the study as a function of stimulation frequency in the 1 kHz to 10 kHz frequency range, including average optimal pulse width (FIG. 10A), mean charge per second and optimal stimulation amplitude (FIG. 10B), and back pain scores (FIG. 10C).

FIG. 13 shows a fitting module showing how the relationships and regions determined relating optimal pulse width and frequency (≤10 kHz) can be used to set sub-perception stimulation parameters for an IPG or ETS.

DETAILED DESCRIPTION

Figure 4:
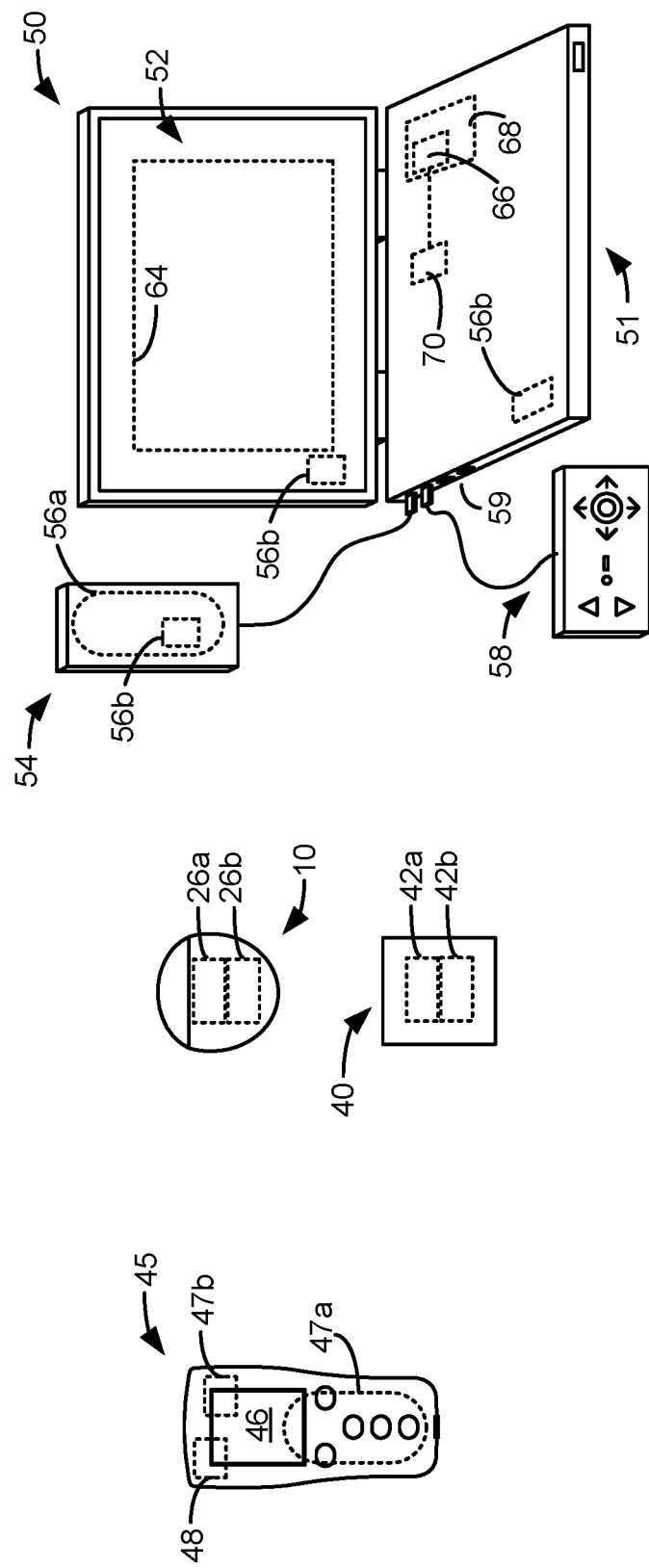
FIG. 4 shows various external devices capable of communicating with and programming stimulation in an IPG and ETS, in accordance with the prior art.

While Spinal Cord Stimulation (SCS) therapy can be an effective means of alleviating a patient's pain, such stimulation can also cause paresthesia. Paresthesia—sometimes referred to a "supra-perception" therapy—is a sensation such as tingling, prickling, heat, cold, etc. that can accompany SCS therapy. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing.

Nonetheless, at least for some patients, SCS therapy would ideally provide complete pain relief without paresthesia—what is often referred to as "sub-perception" or sub-threshold therapy that a patient cannot feel. Effective sub-perception therapy may provide pain relief without paresthesia by issuing stimulation pulses at higher frequencies. Unfortunately, such higher-frequency stimulation may require more power, which tends to drain the battery 14 of the IPG 10. See, e.g., U.S. Patent Application Publication 2016/0367822. If an IPG's battery 14 is a primary cell and not rechargeable, high-frequency stimulation means that the IPG 10 will need to be replaced more quickly. Alternatively, if an IPG battery 14 is rechargeable, the IPG 10 will need to be charged more frequently, or for longer periods of time. Either way, the patient is inconvenienced.

In an SCS application, it is desirable to determine a stimulation program that will be effective for each patient. A significant part of determining an effective stimulation program is to determine a "sweet spot" for stimulation in each patient, i.e., to select which electrodes should be active (E) and with what polarities (P) and relative amplitudes (X %) to recruit and thus treat a neural site at which pain originates in a patient. Selecting electrodes proximate to this neural site of pain can be difficult to determine, and experimentation is typically undertaken to select the best combination of electrodes to provide a patient's therapy.

As described in U.S. Patent Application Publication 2019/0366104, which is hereby expressly incorporated by reference, selecting electrodes for a given patient can be even more difficult when sub-perception therapy is used, because the patient does not feel the stimulation, and therefore it can be difficult for the patient to feel whether the stimulation is "covering" his pain and therefore whether selected electrodes are effective. Further, sub-perception stimulation therapy may require a "wash in" period before it can become effective. A wash in period can take up to a day or more, and therefore sub-perception stimulation may not be immediately effective, making electrode selection more difficult.

FIG. 6 briefly explains the '539 Application's technique for a sweet spot search, i.e., how electrodes can be selected that are proximate to a neural site of pain 298 in a patient, when sub-perception stimulation is used. The technique of FIG. 6 is particularly useful in a trial setting after a patient is first implanted with an electrode array, i.e., after receiving their IPG or ETS.

In the example shown, it is assumed that a pain site 298 is likely within a tissue region 299. Such region 299 may be deduced by a clinician based on the patient symptoms, e.g., by understanding which electrodes are proximate to certain vertebrae (not shown), such as within the T9-T10 interspace. In the example shown, region 299 is bounded by electrodes E2, E7, E15, and E10, meaning that electrodes outside of this region (e.g., E1, E8, E9, E16) are unlikely to have an effect on the patient's symptoms. Therefore, these electrodes may not be selected during the sweet spot search depicted in FIG. 6, as explained further below.

In FIG. 6, a sub-perception bipole 297a is selected, in which one electrode (e.g., E2) is selected as an anode that will source a positive current (+A) to the patient's tissue, while another electrode (e.g., E3) is selected as a cathode that will sink a negative current (−A) from the tissue. This is similar to what was illustrated earlier with respect to FIG. 2, and biphasic stimulation pulses can be used employing active charge recovery. Because the bipole 297a provides sub-perception stimulation, the amplitude A used during the sweet spot search is titrated down until the patient no longer feels paresthesia. This sub-perception bipole 297a is provided to the patient for a duration, such as a few days, which allows the sub-perception bipole's potential effectiveness to "wash in," and allows the patient to provide feedback concerning how well the bipole 297a is helping their symptoms. Such patient feedback can comprise a pain scale ranking. For example, the patient can rank their pain on a scale from 1-10 using a Numerical Rating Scale (NRS) or the Visual Analogue Scale (VAS), with 1 denoting no or little pain and 10 denoting a worst pain imaginable. As discussed in the '539 Application, such pain scale ranking can be entered into the patient's external controller 45.

After the bipole 297a is tested at this first location, a different combination of electrodes is chosen (anode electrode E3, cathode electrode E4), which moves the location of the bipole 297 in the patient's tissue. Again, the amplitude of the current A may need to be titrated to an appropriate sub-perception level. In the example shown, the bipole 297a is moved down one electrode lead, and up the other, as shown by path 296 in the hope of finding a combination of electrodes that covers the pain site 298. In the example of FIG. 6, given the pain site 298's proximity to electrodes E13 and E14, it might be expected that a bipole 297a at those electrodes will provide the best relief for the patient, as reflected by the patient's pain score rankings. The particular stimulation parameters chosen when forming bipole 297a can be selected at the GUI 64 of the clinician programmer 50 or other external device (such as a patient external controller 45) and wirelessly telemetered to the patient's IPG or ETS for execution.

While the sweet spot search of FIG. 6 can be effective, it can also take a significantly long time when sub-perception stimulation is used. As noted, sub-perception stimulation is provided at each bipole 297 location for a number of days, and because a large number of bipole locations are chosen, the entire sweep spot search can take up to a month to complete.

The inventors have determined via testing of SCS patients that even if it is desired to eventually use sub-perception therapy for a patient going forward after the sweet spot search, it is beneficial to use supra-perception stimulation during the sweet spot search to select active electrodes for the patient. Use of supra-perception stimulation during the sweet spot search greatly accelerates determination of effective electrodes for the patient compared to the use of sub-perception stimulation, which requires a wash in period at each set of electrodes tested. After determining electrodes for use with the patient using supra-perception therapy, therapy may be titrated to sub-perception levels keeping the same electrodes determined for the patient during the sweet spot search. Because the selected electrodes are known to be recruiting the neural site of the patient's pain, the application of sub-perception therapy to those electrodes is more likely to have immediate effect, reducing or potentially eliminating the need to wash in the sub-perception therapy that follows. In short, effective sub-perception therapy can be achieved more quickly for the patient when supra-perception sweet spot searching is utilized. Preferably, supra-perception sweet spot searching occurs using symmetric biphasic pulses occurring at low frequencies—such as between 40 and 200 Hz in one example.

In accordance with one aspect of the disclosed technique, a patient will be provided sub-perception therapy. Sweet spot searching to determine electrodes that may be used during sub-perception therapy may precede such sub-perception therapy. In some aspects, when sub-perception therapy is used for the patient, sweet spot searching may use a bipole 297a that is sub-perception (FIG. 6), as just described. This may be relevant because the sub-perception sweet spot search may match the eventual sub-perception therapy the patient will receive.

However, the inventors have determined that even if sub-perception therapy is eventually to be used for the patient, it can be beneficial to use supra-perception stimulation—that is, stimulation with accompanying paresthesia—during the sweet spot search. This is shown in FIG. 7A, where the movable bipole 301a provides supra-perception stimulation that can be felt by the patient. Providing bipole 301a as supra-perception stimulation can merely involve increasing its amplitude (e.g., current A) when compared to the sub-perception bipole 297a of FIG. 6, although other stimulation parameters might be adjusted as well, such as by providing longer pulse widths.

The inventors have determined that there are benefits to employing supra-perception stimulation during the sweet spot search even though sub-perception therapy will eventually be used for the patient.

First, as mentioned above, the use of supra-perception therapy by definition allows the patient to feel the stimulation, which enables the patient to provide essentially immediate feedback to the clinician whether the paresthesia seems to be well covering his pain site 298. In other words, it is not necessary to take the time to wash in bipole 301a at each location as it is moved along path 296. Thus, a suitable bipole 301a proximate to the patient's pain site 298 can be established much more quickly, such as within a single clinician's visit, rather than over a period of days or weeks. In one example, when sub-perception therapy is preceded with supra-perception sweet spot searching, the time needed to wash in the sub-perception therapy can be one hour or less, ten minutes or less, or even a matter of seconds. This allows wash in to occur during a single programming session during which the patient's IPG or ETS is programmed, and without the need for the patient to leave the clinician's office.

Second, use of supra-perception stimulation during the sweet spot search ensures that electrodes are determined that well recruit the pain site 298. As a result, after the sweet spot search is complete and eventual sub-perception therapy is titrated for the patient, wash in of that sub-perception therapy may not take as long because the electrodes needed for good recruitment have already been confidently determined.

Figure 7B:
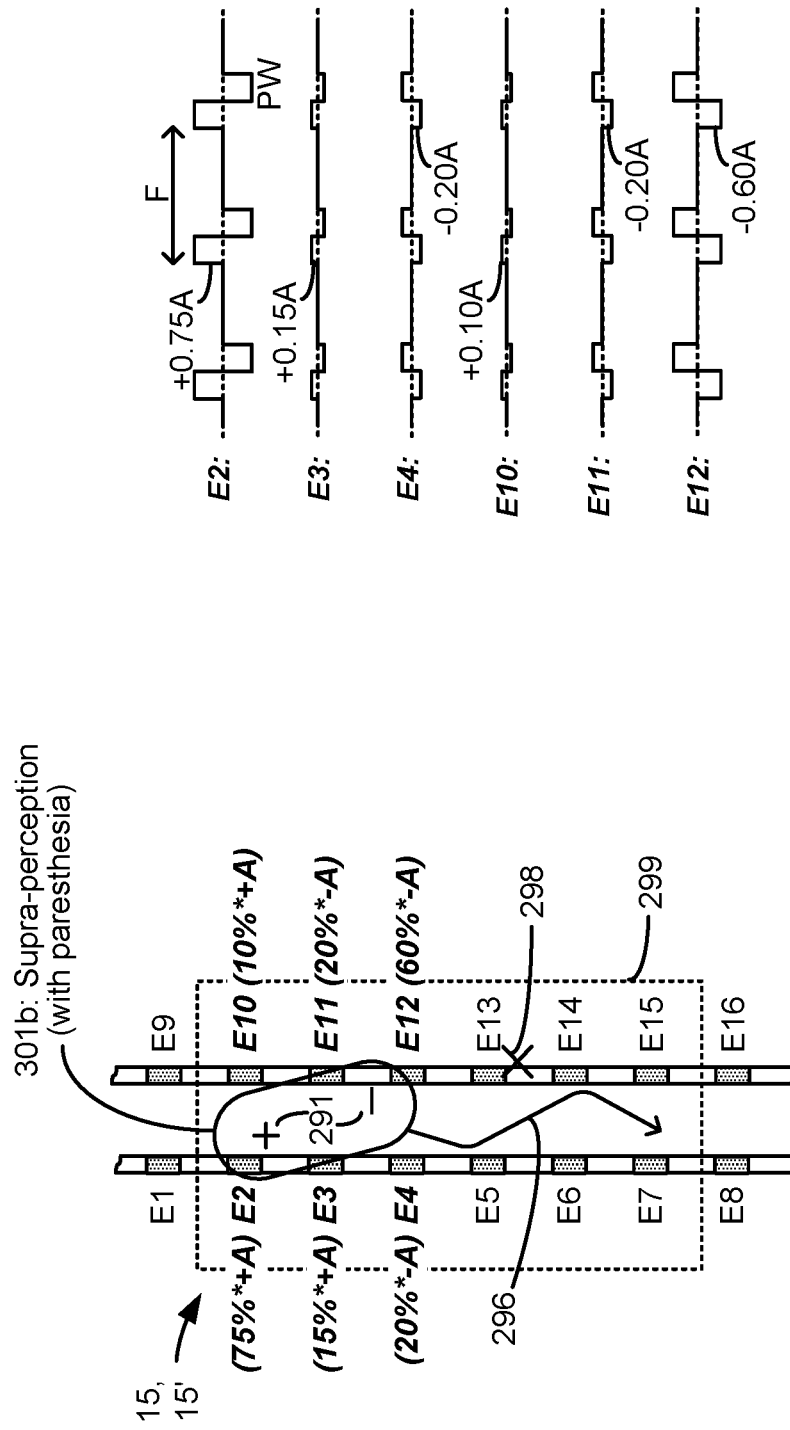

FIGS. 7B-7D show other supra-perception bipoles 301b-301d that may be used, and in particular show how the virtual bipoles may be formed using virtual poles by activating three or more of the electrodes 16. Virtual poles are discussed further in U.S. Patent Application Publication 2019/0175915, which is incorporated herein by reference in its entirety, and thus virtual poles are only briefly explained here. Forming virtual poles is assisted if the stimulation circuitry 28 or 44 used in the IPG or ETS is capable of independently setting the current at any of the electrodes—what is sometimes known as a Multiple Independent Current Control (MICC), which is explained further below with reference to FIG. 8.

When a virtual bipole is used, the GUI 64 (FIG. 5) of the clinician programmer 50 (FIG. 4) can be used to define an anode pole (+) and a cathode pole (−) at positions 291 (FIG. 7B) that may not necessarily correspond to the position of the physical electrodes 16. The control circuitry 70 in the clinician programmer 50 can compute from these positions 291 and from other tissue modeling information which physical electrodes 16 will need to be selected and with what amplitudes to form the virtual anode and virtual cathode at the designated positions 291. As described earlier, amplitudes at selected electrodes may be expressed as a percentage X % of the total current amplitude A specified at the GUI 64 of the clinician programmer 50.

For example, in FIG. 7B, the virtual anode pole is located at a position 291 between electrodes E2, E3 and E10. The clinician programmer 50 may then calculate based on this position that each of these electrodes (during first pulse phase 30a) will receive an appropriate share (X %) of the total anodic current +A to locate the virtual anode at this position. Since the virtual anode's position is closest to electrode E2, this electrode E2 may receive the largest share of the specified anodic current +A (e.g., 75%*+A). Electrodes E3 and E10 which are proximate to the virtual anode pole's position but farther away receive lesser shares of the anodic current (e.g., 15%*+A and 10%*+A respectively). Likewise, it can be seen that from the designated position 291 of the virtual cathode pole, which is proximate to electrodes E4, E11, and E12, that these electrodes will receive an appropriate share of the specified cathodic current −A (e.g., 20%*−A, 20%*−A, and 60%*−A respectively, again during the first pulse phase 30a). These polarities would then be flipped during the second phases 30b of the pulses, as shown in the waveforms of FIG. 7B. In any event, the use of virtual poles in the formation of bipole 301b allows the field in the tissue to be shaped, and many different combinations of electrodes can be tried during the sweet spot search. In this regard, it is not strictly necessary that the (virtual) bipole be moved along an orderly path 296 with respect to the electrodes, and the path may be randomized, perhaps as guided by feedback from the patient.

FIG. 7C shows a useful virtual bipole 301c configuration that can be used during the sweet spot search. This virtual bipole 301c again defines a target anode and cathode whose positions do not correspond to the position of the physical electrodes. The virtual bipole 301c is formed along a lead— essentially spanning the length of four electrodes from E1 to E5. This creates a larger field in the tissue better able to recruit the patient's pain site 298. This bipole configuration 301c may need to be moved to a smaller number of locations than would a smaller bipole configuration compared 301a of FIG. 7A as it moves along path 296, thus accelerating pain site 298 detection. FIG. 7D expands upon the bipole configuration of FIG. 7C to create a virtual bipole 301d using electrodes formed on both leads, e.g., from electrodes E1 to E5 and from electrodes E9 to E13. This bipole 301d configuration need only be moved along a single path 296 that is parallel to the leads, as its field is large enough to recruit neural tissue proximate to both leads. This can further accelerate pain site detection.

In some aspects, the supra-perception bipoles 301a-301d used during the sweet spot search comprise symmetric biphasic waveforms having actively-driven (e.g., by the stimulation circuitry 28 or 44) pulse phases 30a and 30b of the same pulse width PW and the same amplitude (with the polarity flipped during the phases) (e.g., $A_{30a}=A_{30b}$, and $PW_{30a}=PW_{30b}$). This is beneficial because the second pulse phase 30b provides active charge recovery, with in this case the charge provided during the first pulse phase 30a ($Q_{30a}$) equaling the charge of the second pulse phase 30b ($Q_{30b}$), such that the pulses are charge balanced. Use of biphasic waveforms are also believed beneficial because, as is known, the cathode is largely involved in neural tissue recruitment. When a biphasic pulse is used, the positions of the (virtual) anode and cathode will flip during the pulse's two phases. This effectively doubles the neural tissue that is recruited for stimulation, and thus increases the possibility that the pain site 298 will be covered by a bipole at the correct location.

The supra-perception bipoles 301a-301d do not however need to comprise symmetric biphasic pulses as just described. For example, the amplitude and pulse width of the two phases 30a and 30b can be different, while keeping the charge (Q) of the two phases balanced (e.g., $Q_{30a}=A_{30a}*PW_{30a}=A_{30b}*PW_{30b}=Q_{30b}$). Alternatively, the two phases 30a and 30b may be charge imbalanced (e.g., $Q_{30a}=A_{30a}*PW_{30a}>A_{30b}*PW_{30b}=Q_{30b}$, or $Q_{30a}=A_{30a}*PW_{30a}<A_{30b}*PW_{30b}=Q_{30b}$). In short, the pulses in bipoles 301-301d can be biphasic symmetric (and thus inherently charge balanced), biphasic asymmetric but still charge balanced, or biphasic asymmetric and charge imbalanced.

In a preferred example, the frequency F of the supra-perception pulses 301a-301d used during the supra-perception sweet spot search may be 10 kHz or less, 1 kHz or less, 500 Hz or less, 300 Hz or less, 200 Hz or less, 130 Hz or less, or 100 Hz or less, or ranges bounded by two of these frequencies (e.g., 100-130 Hz, or 100-200 Hz). In particular examples, frequencies of 90 Hz, 40 Hz, or 10 Hz can be used, with pulses comprising biphasic pulses which are preferably symmetric. However, a single actively-driven pulse phase followed by a passive recovery phase could also be used. The pulse width PW may also comprise a value in the range of hundreds of microseconds, such as 150 to 400 microseconds. Because the goal of supra-perception sweet spot searching is merely to determine electrodes that appropriately cover a patient's pain, frequency and pulse width may be of less importance at this stage. Once electrodes have been chosen for sub-perception stimulation, frequency and pulse width can be optimized, as discussed further below.

It should be understood that the supra-perception bipoles 301a-301d used during sweet spot searching need not necessarily be the same electrodes that are selected when later providing the patient with sub-perception therapy. Instead, the best location of the bipole noticed during the search can be used as the basis to modify the selected electrodes. Suppose for example that a bipole 301a (FIG. 7A) is used during sweep spot searching, and it is determined that bipole provides the best pain relief when located at electrodes E13 and E14. At that point, sub-perception therapy using those electrodes E13 and E14 can be tried for the patient going forward. Alternatively, it may be sensible to modify the selected electrodes to see if the patient's symptoms can be further improved before sub-perception therapy is tried. For example, the distance (focus) between the cathode and anode can be varied, using virtual poles as already described. Or, a tripole (anode/cathode/anode) consisting of electrodes E12/E13/E14 or E13/E14/E15 could be tried. See U.S. Patent Application Publication 2019/0175915 (discussing tripoles). Or electrodes on a different lead could also be tried in combination with E13 and E14. For example, because electrodes E5 and E6 are generally proximate to electrodes E13 and E14, it may be useful to add E5 or E6 as sources of anodic or cathodic current (again creating virtual poles). All of these types of adjustments should be understood as comprising "steering" or an adjustment to the "location" at which therapy is applied, even if a central point of stimulation doesn't change (as can occur for example when the distance or focus between the cathode and anode is varied).

Figure 8:
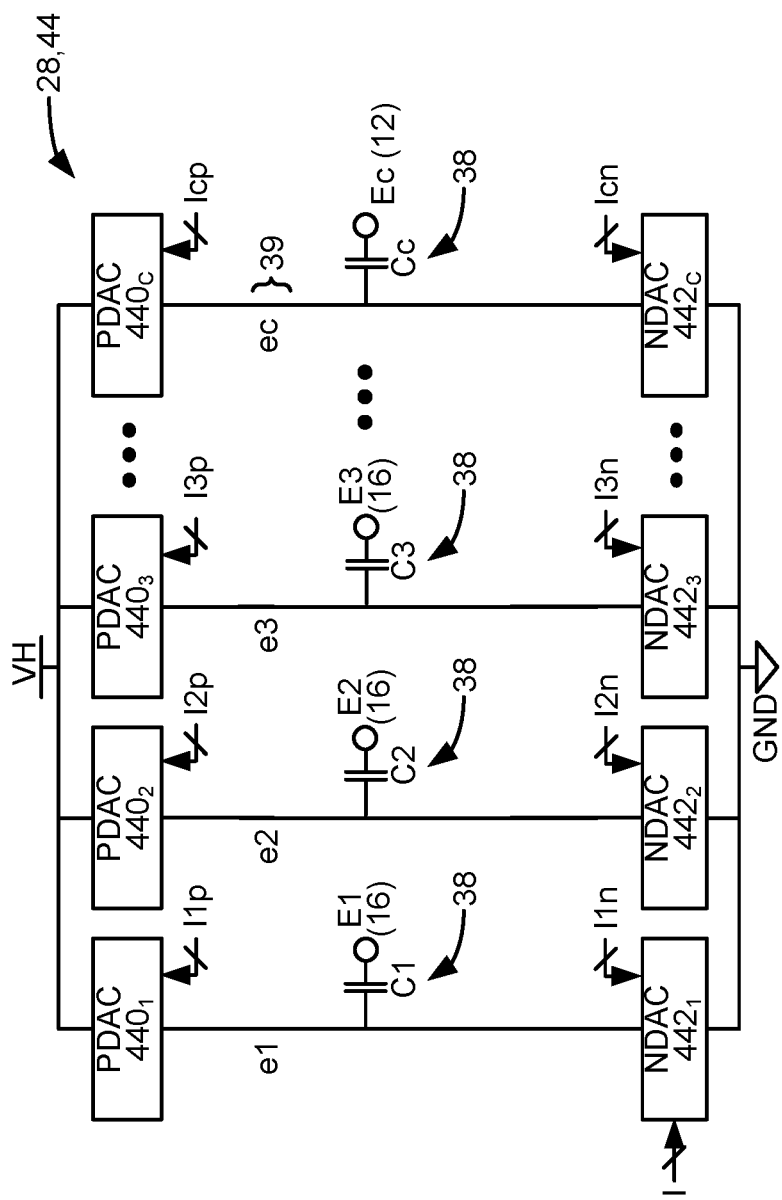
FIG. 8 shows stimulation circuitry useable in the IPG or ETS capable of providing Multiple Independent Current Control to independently set the current at each of the electrodes.

Multiple Independent Current Control (MICC) is explained in one example with reference to FIG. 8, which shows the stimulation circuitry 28 (FIG. 1) or 44 (FIG. 3) in the IPG or ETS used to form prescribed stimulation at a patient's tissue. The stimulation circuitry 28 or 44 can control the current or charge at each electrode independently, and using GUI 64 (FIG. 5) allows the current or charge to be steered to different electrodes, which is useful for example when moving the bipole 301i along path 296 during the sweet spot search (FIG. 7A-7D). The stimulation circuitry 28 or 44 includes one or more current sources $440_i$, and one or more current sinks $442_i$. The sources and sinks $440_i$ and $442_i$ can comprise Digital-to-Analog converters (DACs), and may be referred to as PDACs $440_i$ and NDACs $442_i$ in accordance with the Positive (sourced, anodic) and Negative (sunk, cathodic) currents they respectively issue. In the example shown, a NDAC/PDAC $440_i/442_i$ pair is dedicated (hardwired) to a particular electrode node ei 39. Each electrode node ei 39 is preferably connected to an electrode Ei 16 via a DC-blocking capacitor Ci 38, which act as a safety measure to prevent DC current injection into the patient, as could occur for example if there is a circuit fault in the stimulation circuitry 28 or 44. PDACs $440_i$ and NDACs $442_i$ can also comprise voltage sources.

Proper control of the PDACs $440_i$ and NDACs $442_i$ via GUI 64 allows any of the electrodes 16 and the case electrode Ec 12 to act as anodes or cathodes to create a current through a patient's tissue. Such control preferably comes in the form of digital signals Iip and Iin that set the anodic and cathodic current at each electrode Ei. If for example it is desired to set electrode E1 as an anode with a current of +3 mA, and to set electrodes E2 and E3 as cathodes with a current of −1.5 mA each, control signal I1p would be set to the digital equivalent of 3 mA to cause PDAC $440_1$ to produce +3 mA, and control signals I2n and I3n would be set to the digital equivalent of 1.5 mA to cause NDACs $442_2$ and $442_3$ to each produce −1.5 mA. Note that definition of these control signals can also occur using the programmed amplitude A and percentage X % set in the GUI 64. For example, A may be set to 3 mA, with E1 designated as an anode with X=100 %, and with E2 and E3 designated at cathodes with X=50%. Alternatively, the control signals may not be set with a percentage, and instead the GUI 64 can simply prescribe the current that will appear at each electrode at any point in time.

In short, the GUI 64 may be used to independently set the current at each electrode, or to steer the current between different electrodes. This is particularly useful in forming virtual bipoles, which as explained earlier involve activation of more than two electrodes. MICC also allows more sophisticated electric fields to be formed in the patient's tissue.

Other stimulation circuitries 28 can also be used to implement MICC. In an example not shown, a switching matrix can intervene between the one or more PDACs $440_i$ and the electrode nodes ei 39, and between the one or more NDACs $442_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, and U.S. Patent Application Publications 2018/0071513, 2018/0071520, and 2019/0083796.

Much of the stimulation circuitry 28 or 44, including the PDACs $440_i$ and NDACs $442_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with the IPG's or ETS's telemetry antennas), circuitry for generating the compliance voltage VH that powers the stimulation circuitry, various measurement circuits, etc.

While it is preferred to use sweet spot searching, and in particular supra-perception sweet spot searching, to determine the electrodes to be used during subsequent sub-perception therapy, it should be noted that this is not strictly necessary. Sub-perception therapy can be preceded by sub-perception sweet spot searching, or may not be preceded by sweet spot searching at all. In short, sub-perception therapy as described next is not reliant on the use of any sweet spot search.

In another aspect of the invention, the inventors have determined via testing of SCS patients that statistically significant correlations exists between pulse width (PW) and frequency (F) where an SCS patient will experience a reduction in back pain without paresthesia (sub-perception). Use of this information can be helpful in deciding what pulse width is likely optimal for a given SCS patient based on a particular frequency, and in deciding what frequency is likely optimal for a given SCS patient based on a particular pulse width. Beneficially, this information suggests that paresthesia-free sub-perception SCS stimulation can occur at frequencies of 10 kHz and below. Use of such low frequencies allows sub-perception therapy to be used with much lower power consumption in the patient's IPG or ETS.

Figure 9:
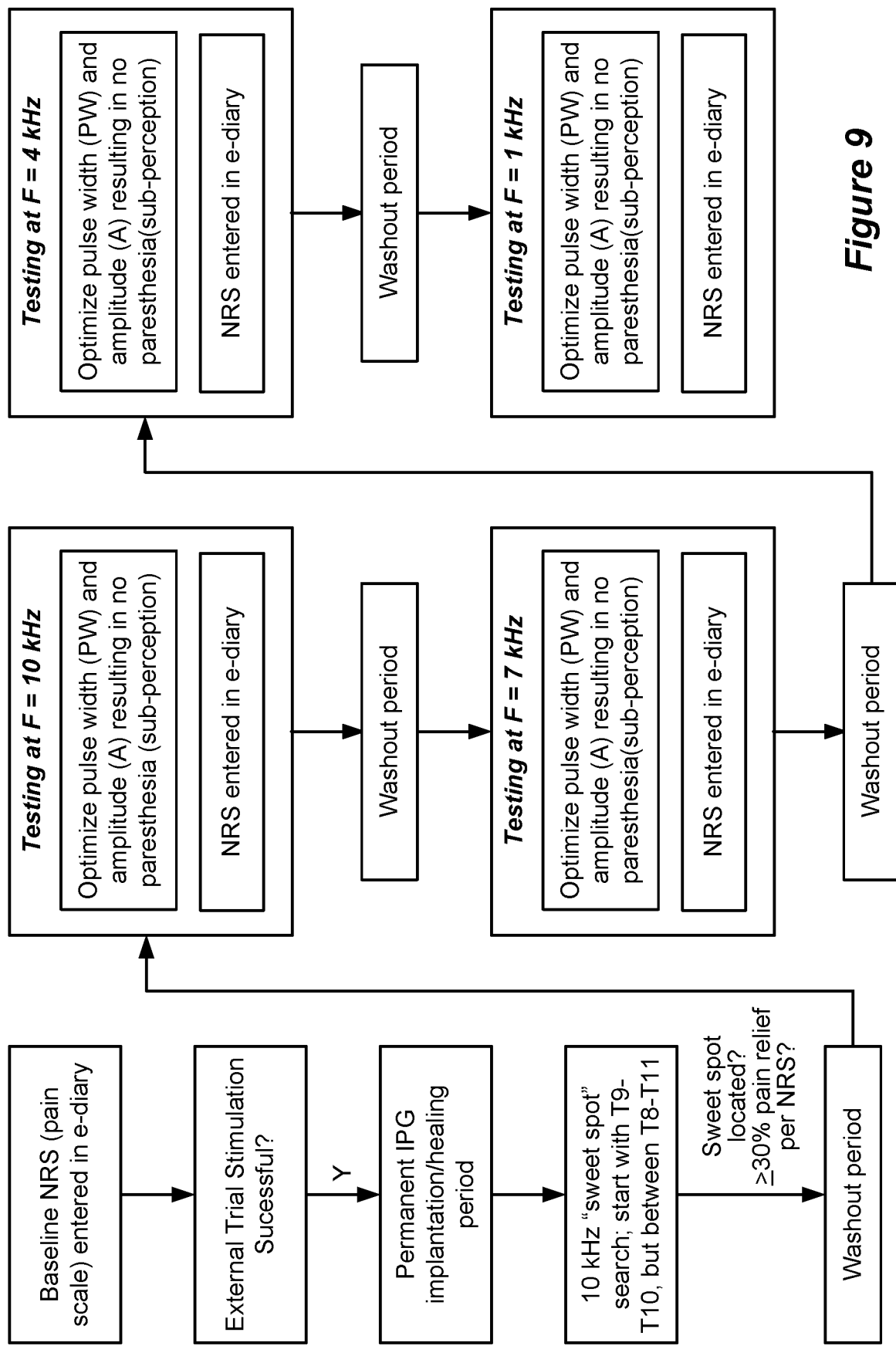
FIG. 9 shows a flow chart of a study conducted on various patients with back pain designed to determine optimal sub-perception SCS stimulation parameters over a frequency range of 1 kHz to 10 kHz.

FIGS. 9-11C shows results derived from testing patients at frequencies within a range of 1 kHz to 10 kHz. FIG. 9 explains how data was gathered from actual SCS patients, and the criteria for patient inclusion in the study. Patients with back pain, but not yet receiving SCS therapy, were first identified. Key patient inclusion criteria included having persistent lower back pain for greater than 90 days; a NRS pain scale of 5 or greater (NRS is explained below); stable opioid medications for 30 days; and a Baseline Oswestry Disability index score of greater than or equal to 20 and lower than or equal to 80. Key patient exclusion criteria included having back surgery in the previous 6 months; existence of other confounding medical/psychological conditions; and untreated major psychiatric comorbidity or serious drug related behavior issues.

Figure 5:
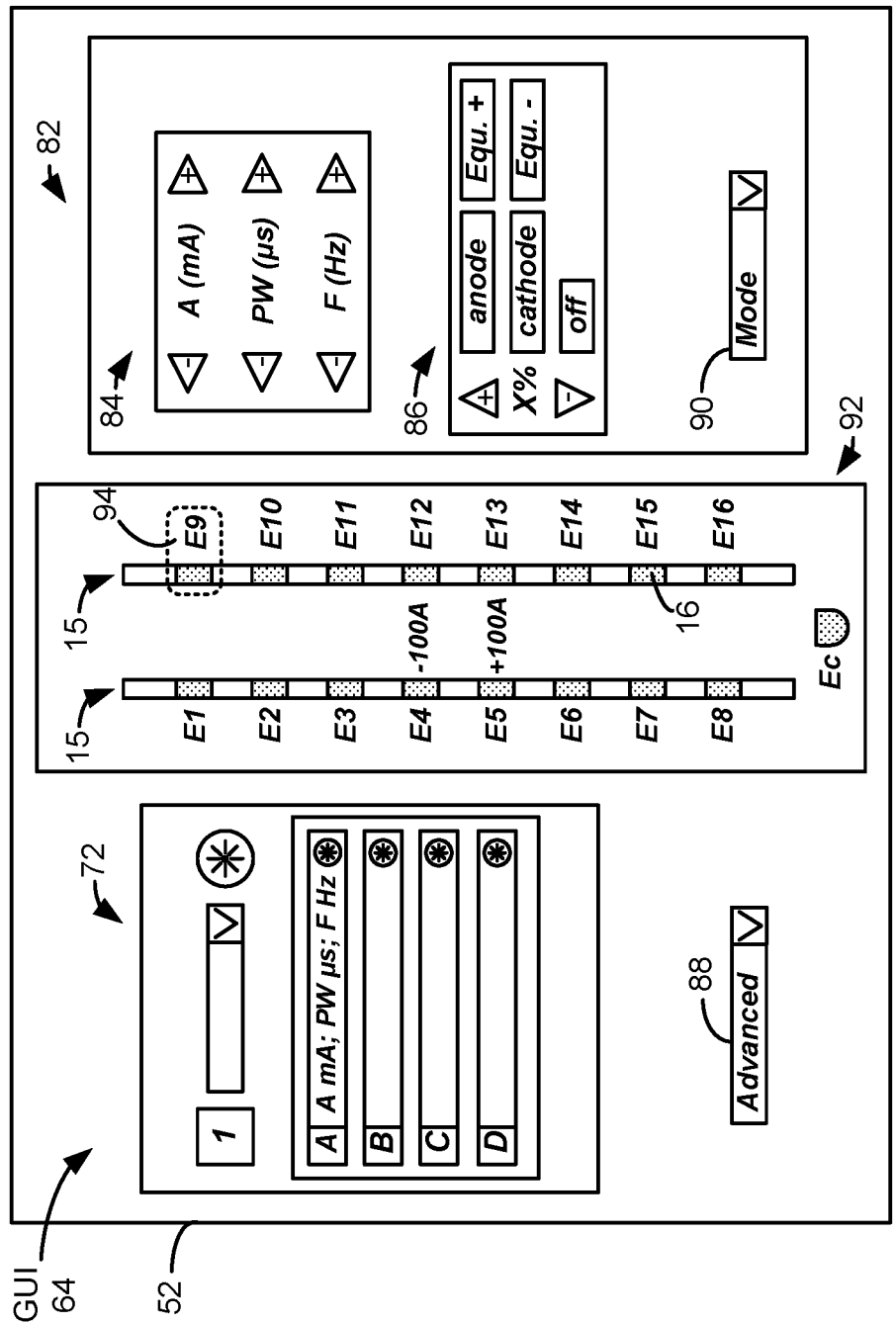
FIG. 5 shows a Graphical User Interface (GUI) of a clinician programmer external device for setting or adjusting stimulation parameters, in accordance with the prior art.

After such initial screening, patients periodically entered a qualitative indication of their pain (i.e., a pain score) into a portable e-diary device, which can comprise a patient external controller 45, and which in turn can communicate its data to a clinician programmer 50 (FIG. 4). Such pain scores can comprise a Numerical Rating Scale (NRS) score from 1-10, and were input to the e-diary three times daily. As shown in FIG. 10C, the baseline NRS score for patients not eventually excluded from the study and not yet receiving sub-perception stimulation therapy was approximately 6.75/10, with a standard error, SE (sigma/SQRT(n)) of 0.25.

Returning to FIG. 9, patients then had trial leads 15' (FIG. 3) implanted on the left and right sides of the spinal column, and were provided external trial stimulation as explained earlier. A clinician programmer 50 was used to provide a stimulation program to each patient's ETS 40 as explained earlier. This was done to make sure that SCS therapy was helpful for a given patient to alleviate their pain. If SCS therapy was not helpful for a given patient, trial leads 15' were explanted, and that patient was then excluded from the study.

Those patients for whom external trial stimulation was helpful eventually received full implantation of a permanent IPG 10, as described earlier. After a healing period, and again using clinician programmer 50, a "sweet spot" for stimulation was located in each patient, i.e., which electrodes should be active (E) and with what polarities (P) and relative amplitudes (X %) to recruit and thus treat a site 298 of neural site in the patient. The sweet spot search can occur in any of the manners described earlier with respect to FIGS. 6-7D, but in a preferred embodiment would comprise supra-perception stimulation (e.g., e.g., 7A-7D) because of the benefits described earlier. However, this is not strictly necessary, and sub-perception stimulation can also be used during the sweet spot search. In the example of FIG. 9, sweet spot searching occurred at 10 kHz, but again the frequency used during the sweet spot search can be varied. Symmetric biphasic pulses were used during sweet spot searching, but again, this is not strictly required. Deciding which electrodes should be active started with selecting electrodes 16 present between thoracic vertebrae T9 and T10. However, electrodes as far away as T8 and T11 were also activated if necessary. Which electrodes were proximate to vertebrae T8, T9, T10, and T1 was determined using fluoroscopic images of the leads 15 within each patient.

During sweet spot searching, bipolar stimulation using only two electrodes was used for each patient, and using only adjacent electrodes on a single lead 15, similar to what was described in FIGS. 6 and 7A. Thus, one patient's sweet spot might involve stimulating adjacent electrodes E4 as cathode and E5 as anode on the left lead 15 as shown earlier in FIG. 2 (which electrodes may be between T9 and T10), while another patient's sweet spot might involve stimulating adjacent electrodes E9 as anode and E10 as cathode on the right lead 15 (which electrodes may be between T10 and T11). Using only adjacent-electrode bipolar stimulation and only between vertebrae T8 to T11 was desired to minimize variance in the therapy and pathology between the different patients in the study. However, more complicated bipoles such as those described with respect to FIGS. 7B-7D could also be used during sweet spot searching. If a patient had sweet spot electrodes in the desired thoracic location, and if they experienced a 30% or greater pain relief per an NRS score, such patients were continued in the study; patients not meeting these criteria were excluded from further study. While the study started initially with 39 patients, 19 patients were excluded from study up to this point in FIG. 9, leaving a total of 20 patients remaining.

The remaining 20 patients were then subjected to a "washout" period, meaning their IPGs did not provide stimulation for a time. Specifically, patients' NRS pain scores were monitored until their pain reached 80% of their initial baseline pain. This was to ensure that previous benefits of stimulation did not carry over to a next analysis period.

Thereafter, remaining patients were subjected to sub-perception SCS therapy at different frequencies in the range from 1 kHz to 10 kHz using the sweet spot active electrodes determined earlier. This however isn't strictly necessary, because as noted earlier the current at each electrode could also be independently controlled to assist in shaping of the electric filed in the tissue. As shown in FIG. 9, the patients were each tested using stimulation pulses with frequencies of 10 kHz, 7 kHz, 4 kHz, and 1 kHz. FIG. 9 for simplicity shows that these frequencies were tested in this order for each patient, but in reality the frequencies were applied to each patient in random orders. Testing at a given frequency, once complete, was followed by a washout period before testing at another frequency began.

At each tested frequency, the amplitude (A) and pulse width (PW) (first pulse phase 30a; FIG. 2) of the stimulation was adjusted and optimized for each patient such that each patient experienced good pain relief possible but without paresthesia (sub-perception). Specifically, using clinician programmer 50, and keeping as active the same sweet spot electrodes determined earlier (although again this isn't strictly necessary), each patient was stimulated at a low amplitude (e.g., 0), which amplitude was increased to a maximum point (perception threshold) where paresthesia was noticeable by the patient. Initial stimulation was then chosen for the patient at 50% of that maximum amplitude, i.e., such that stimulation was sub-perception and hence paresthesia free. However, other percentages of the maximum amplitude (80%, 90%, etc.) could be chosen as well, and can vary with patient activity or position, as explained further below. In one example, the stimulation circuitry 28 or 44 in the IPG or ETS is configurable to receive an instruction from the GUI 64 via a selectable option (not shown) to reduce the amplitude of the stimulation pulses to or by a set amount or percentage to render the so that the pulses can be made sub-perception if they are not already. Other stimulation parameters may also be reduced (e.g., pulse width, charge) to the same effect.

The patient would then leave the clinician's office, and thereafter and in communication with the clinician (or her technician or programmer) would make adjustments to his stimulation (amplitude and pulse width) using his external controller 45 (FIG. 4). At the same time, the patient would enter NRS pain scores in his e-diary (e.g., the external controller), again three times a day. Patient adjustment of the amplitude and pulse width was typically an iterative process, but essentially adjustments were attempted based on feedback from the patient to adjust the therapy to decrease their pain while still ensuring that stimulation was sub-perception. Testing at each frequency lasted about three weeks, and stimulation adjustments might be made every couple of days or so. At the end of the testing period at a given frequency, optimal amplitude and pulse widths had been determined and were logged for each patient, along with patient NRS pain scores for those optimal parameters as entered in their e-diaries.

In one example, the percentage of the maximum amplitude used to provide sub-perception stimulation could be chosen dependent on an activity level or position of the patient. In regard, the IPG or ETS can include means for determining patient activity or position, such as an accelerometer. If the accelerometer indicates a high degree of patient activity or a position where the electrodes would be farther away from the spinal cord (e.g., lying down), the amplitude could be increased to a higher percentage to increase the current (e.g., 90% of the maximum amplitude). If the patient is experiencing a lower degree of activity or a position where the electrodes would be closer to the spinal card (e.g., standing), the amplitude can be decreased (e.g., to 50% of the maximum amplitude). Although not shown, the GUI 64 of the external device (FIG. 5) can include an option to set the percentage of the maximum amplitude at which paresthesia become noticeable to the patient, thus allowing the patient to adjust the sub-perception current amplitude.

Preferably, Multiple Independent Current Control (MICC) is used to provide or adjust the sub-perception therapy, as discussed earlier with reference to FIG. 8. This allows the current at each electrode to be independently set, which promotes the steering of current or charge between electrodes, facilitates the formation of virtual bipoles, and more generally allows the electric field to be shaped in the patient's tissue. In particular, MICC, can be used to steer sub-perception therapy to different locations in the electrode array and thus the spinal cord. For example, once a set of sub-perception stimulation parameters has been chosen for the patient, one or more of the stimulation parameters can be changed. Such changes may be warranted or dictated by the therapy location. The physiology of the patient may vary at different vertebral positions, and tissue may be more or less conductive at different therapy locations. Therefore, if the sub-perception therapy location is steered to a new location along the spinal cord (which location change may comprise changing the anode/cathode distance or focus), it may be warranted to adjust at least one of the stimulation parameters, such as amplitude. As noted earlier, making sub-perception adjustment is facilitated, and can occur within a programming session, because a substantial wash in period may not be necessary.

Adjustment to sub-perception therapy can also include varying other stimulation parameters, such as pulse width, frequency, and even the duration of the interphase period (IP) (FIG. 2). The interphase duration can impact the neural dose, or the rate of charge infusion, such that higher sub-perception amplitudes would be used with shorter interphase durations. In one example, the interphase duration can be varied between 0-3 ms. After a washout period, a new frequency was tested, using the same protocol as just described.

The sub-perception stimulation pulses used were symmetric biphasic constant current amplitude pulses, having first and second pulses phases 30a and 30b with the same duration (see FIG. 2). However, constant voltage amplitude pulses could be used as well. Pulses of different shapes (triangles, sine waves, etc.) could also be used. Pre-pulsing—that is, providing a small current prior to providing the actively-driven pulse phase(s)—to affect polarization or depolarization of neural tissue can also occur when providing sub-perception therapy. See, e.g., U.S. Pat. No. 9,008,790, which is incorporated herein by reference.

FIGS. 10A-10C show the results of testing the patients at 10 kHz, 7 kHz, 4 Hz and 1 kHz. Data is shown in each figure as average values for the 20 remaining patients at each frequency, with error bars reflecting standard error (SE) between the patients.

Starting with FIG. 10B, the optimized amplitude A for the 20 remaining patients are shown at the tested frequencies. Interestingly, the optimal amplitude at each frequency was essentially constant—around 3 mA. FIG. 10B also shows the amount of energy expended at each frequency, more specifically a mean charge per second (MCS) (in mC/s) attributable to the pulses. MCS is computed by taking the optimal pulse width (FIG. 10A, discussed next) and multiplying it by the optimal amplitude (A) and the frequency (F), which MCS value can comprise a neural dose. MCS correlates to the current or power that the battery in the IPG 10 must expend to form the optimal pulses. Significantly, the MCS is significantly lower at lower frequencies: for example, the MCS at F=1 kHz is approximately ⅓ of its value at higher frequencies (e.g., F=7 kHz or 10 kHz). This means that optimal SCS therapy—that alleviates back pain without paresthesia—is achievable at lower frequencies like F=1 kHz, with the added benefit of lower power draws that are more considerate of the IPG 10's (or ETS 40's) battery.

FIG. 10A shows optimal pulse width as a function of frequency for the 1 kHz to 10 kHz frequency range tested. As shown, the relationship follows a statistically significant trend: when modeled using linear regression 98a, PW=−8.22F+106, where pulse width is measured in microseconds and frequency is measured in kiloHertz, with a correlation coefficient $R^2$ of 0.974; when modeled using polynomial regression 98b, PW=$0.486F^2$−13.6F+116, again with pulse width measured in microseconds and frequency measured in kiloHertz, with an even better correlation coefficient of $R^2$=0.998. Other fitting methods could be used to establish other information relating frequency and pulse width at which stimulation pulses are formed to provide pain relief without paresthesia in the frequency range of 1 kHz to 10 kHz.

Figure 11A:
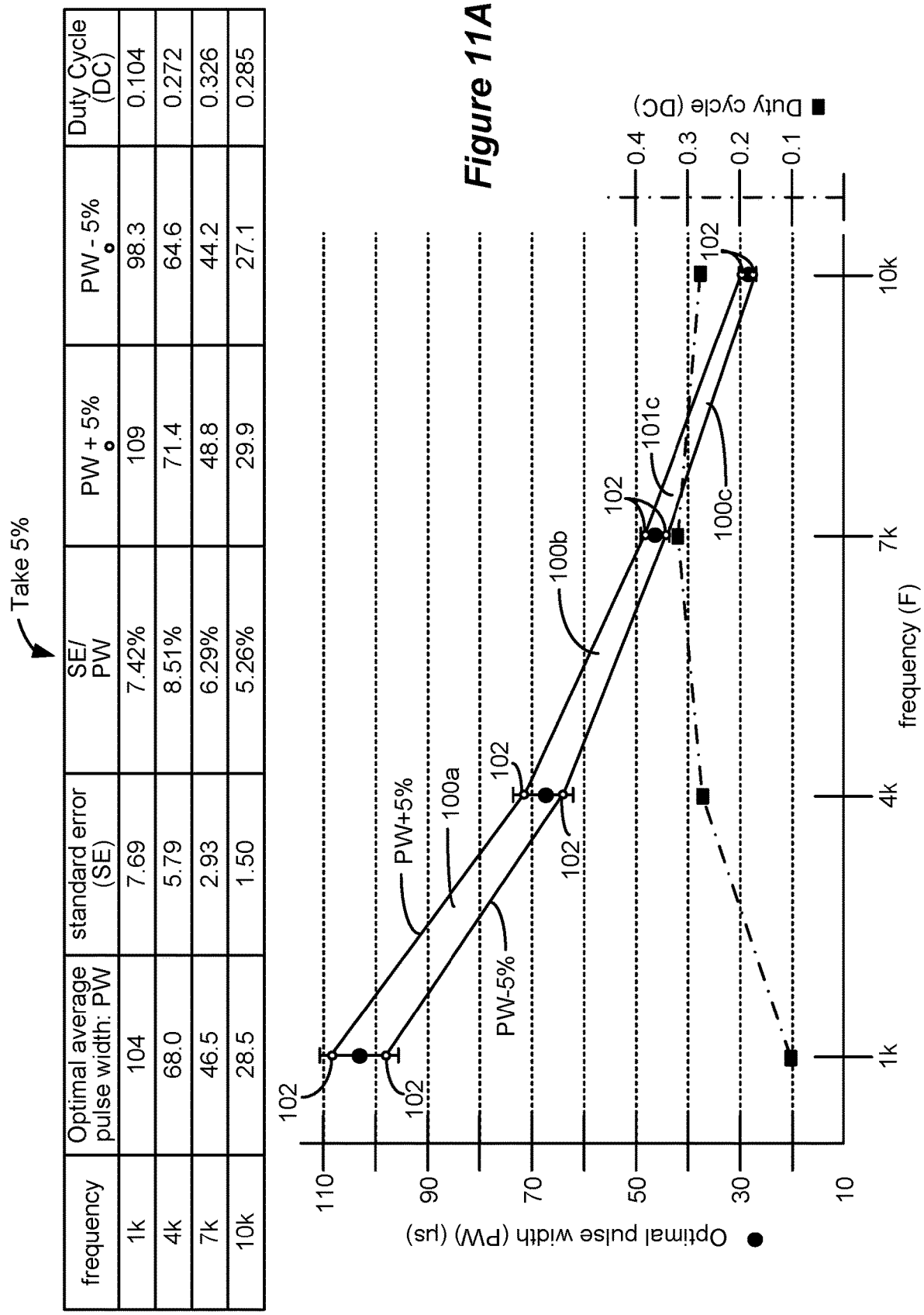
FIGS. 11A-11C shows further analysis of relationships between average optimal pulse width and frequency in the 1 kHz to 10 kHz frequency range, and identifies statistically-significant regions of optimization of these parameters.

Note that the relationship between optimal pulse width and frequency is not simply an expected relationship between frequency and duty cycle (DC), i.e., the duration that a pulse is 'on' divided by its period (1/F). In this regard, notice that a given frequency has a natural effect on pulse width: one would expect that a higher frequency pulses would have smaller pulse widths. Thus, it might be expected for example that a 1 kHz waveform with a 100 microsecond pulse width would have the same clinical results as a 10 kHz waveform with a 10 microsecond frequency, because the duty cycle of both of these waveforms is 10%. FIG. 11A shows the resulting duty cycle of the stimulation waveforms using the optimal pulse width in the frequency range of 1 kHz to 10 kHz. Here, duty cycle is computed by considering the total 'on' time of the first pulse phase 30a (FIG. 2) only; the duration of the symmetric second pulse phase is ignored. This duty cycle is not constant over the 1 kHz to 10 kHz frequency range: for example, the optimal pulse width at 1 kHz (104 microseconds) is not merely ten times the optimal pulse width at 10 kHz (28.5 microseconds). Thus, there is significance to the optimal pulse widths beyond a mere scaling of the frequency.

FIG. 10C shows average patient pain scores at the optimal stimulation parameters (optimal amplitude (FIG. 7B) and pulse width (FIG. 7A)) for each frequency in the range of 1 kHz to 10 kHz. As noted earlier, patients in the study, prior to receiving SCS therapy, initially reported pain scores with an average of 6.75. After SCS implantation and during the study, and with amplitude and pulse width optimized during the provisional of sub-perception therapy, their average pain scores dropped significantly, to an average score of about 3 for all frequencies tested.

FIG. 11A provides a deeper analysis of the resulting relationship between optimal pulse width and frequency in the frequency range of 1 kHz to 10 kHz. The chart in FIG. 11A shows the average optimal pulse width for the 20 patients in the study at each frequency, along with the standard error resulting from variations between them. These are normalized at each frequency by dividing the standard error by the optimal pulse width, ranging in variations at each frequency between 5.26% and 8.51%. From this, a 5% variance (lower than all computed values) can be assumed as a statistically-significant variance at all frequencies tested.

From this 5% variance, a maximum average pulse width (PW+5%) and a minimum average pulse width (PW+5%) can be calculated for each frequency. For example, the optimal average pulse width PW at 1 kHz is 104 microseconds, and 5% above this value (1.05*104 μs) is 109 μs; 5% below this value (0.95*104) is 98.3 μs. Likewise, the optimal average pulse width AVG(PW) at 4 kHz is 68.0 microseconds, and 5% above this value (1.05*68.0 μs) is 71.4 μs; 5% below this value (0.95*68.0 μs) is 64.6 μs. Thus, a statistically-significant reduction in pain without paresthesia occurs in or on the linearly bounded region 100a of points 102 of (1 kHz, 98.3 μs), (1 kHz, 109 μs), (4 kHz, 71.4 μs), and (4 kHz, 64.6 μs). A linearly bounded region 100b around points 102 is also defined for frequencies greater than or equal to 4 kHz and less than or equal to 7 kHz: (4 kHz, 71.4 μs), (4 kHz, 64.6 μs), (7 kHz, 44.2 μs), (7 kHz, 48.8 μs). A linear bounded region 100c around points 102 is also defined for frequencies greater than or equal to 7 kHz and less than or equal to 10 kHz: (7 kHz, 44.2 μs), (7 kHz, 48.8 μs), (10 kHz, 29.9 μs), (10 kHz, 27.1 μs). Such regions 100 thus comprise information relating frequency and pulse width at which stimulation pulses are formed to provide pain relief without paresthesia in the frequency range of 1 kHz to 10 kHz.

Figure 11B:
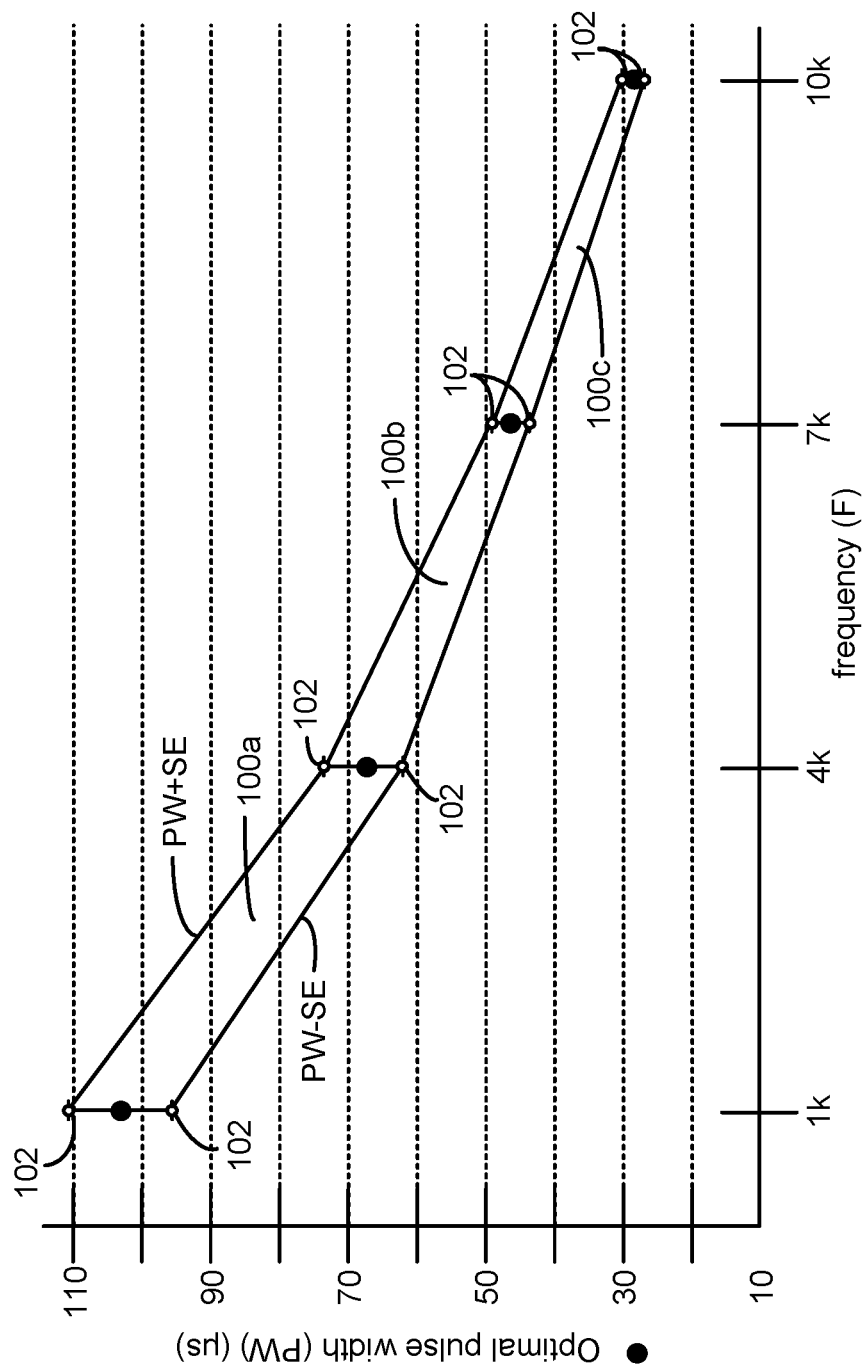

FIG. 11B provides an alternative analysis of the resulting relationship between optimal pulse width and frequency. In this example, regions 100a-100c are defined based upon the standard error (SE) calculated at each frequency. Thus, points 102 defining the corners of the regions 100a-c are simply located at the extent of the SE error bars at each frequency (PW+SE, and PW−SE), even though these error bars are of different magnitudes at each frequency. Thus, a statistically-significant reduction in pain without paresthesia occurs in or on the linearly bounded region 100a of points (1 kHz, 96.3 μs), (1 kHz, 112 μs), (4 kHz, 73.8 μs), and (4 kHz, 62.2 μs). The linear bounded regions 100b and 100c are similar, and because the points 102 defining them are set forth in chart at the top of FIG. 11B, they are not repeated here.

Figure 11C:
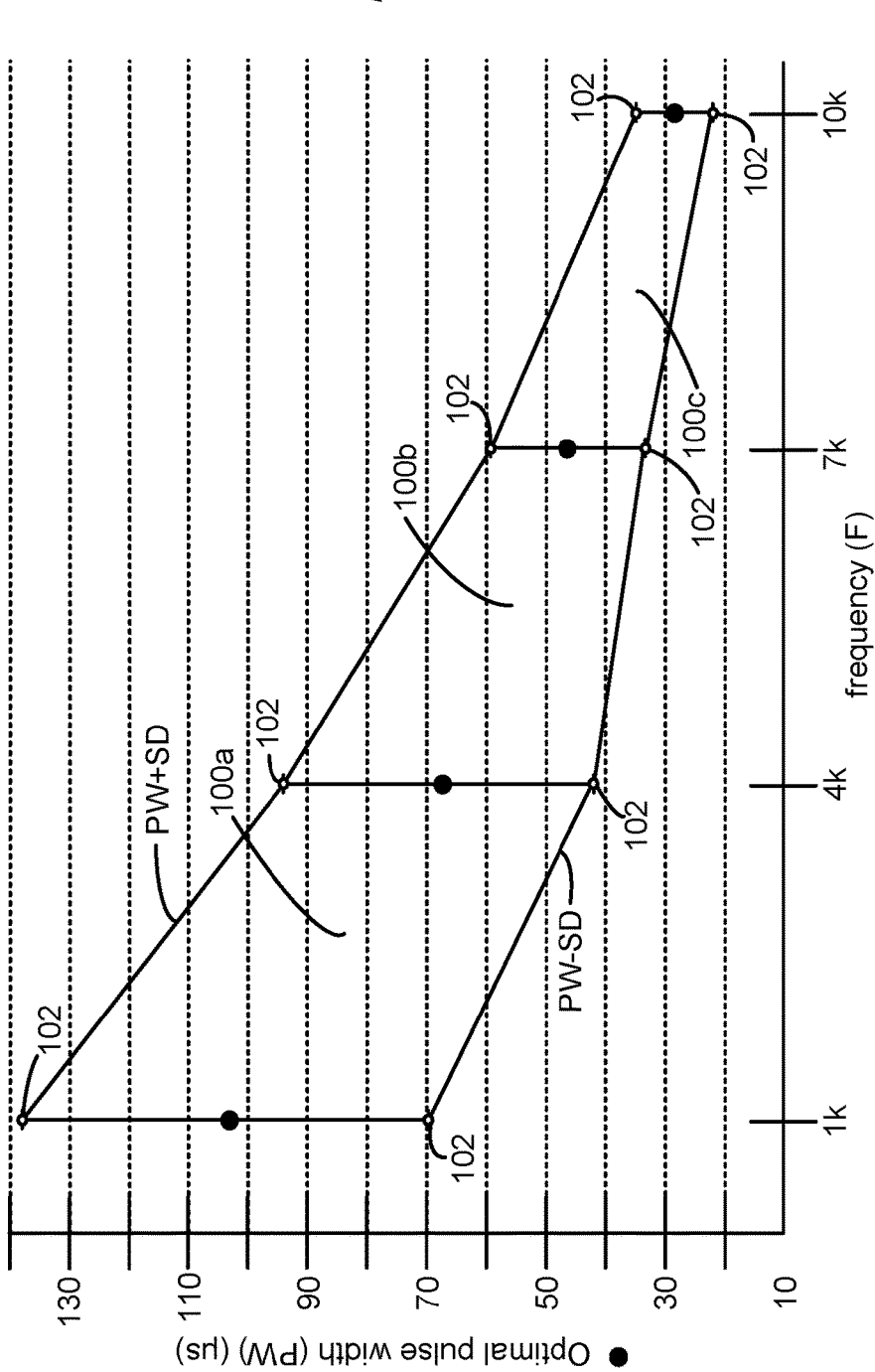

FIG. 11C provides another analysis of the resulting relationship between optimal pulse width and frequency. In this example, regions 100a-100c are defined based upon the standard deviation (SD) calculated at each frequency, which is larger than the standard error (SE) metric used to this point. Points 102 defining the corners of the regions 100a-c are located at the extent of the SD error bars at each frequency (PW+SD, and PW−SD), although points 102 could also be set within the error bars, similar to what was illustrated earlier with respect to FIG. 11A. In any event, a statistically-significant reduction in pain without paresthesia occurs in or on the linearly bounded region 100a of points (1 kHz, 69.6 μs), (1 kHz, 138.4 μs), (4 kHz, 93.9 μs), and (4 kHz, 42.1 μs). The linear bounded regions 100b and 100c are similar, and because the points 102 defining them are set forth in chart at the top of FIG. 11C, they are not repeated here.

More generally, although not illustrated, regions within the frequency range of 1 kHz to 10 kHz where sub-perception efficacy was achieved comprises linearly-bounded region 100a (1 kHz, 50.0 μs), (1 kHz, 200.0 μs), (4 kHz, 110.0 μs), and (4 kHz, 30.0 μs); and/or linearly-bounded region 100b (4 kHz, 110.0 μs), (4 kHz, 30.0 μs), (7 kHz, 30.0 μs), and (7 kHz, 60.0 μs); and/or linearly-bounded region 100c (7 kHz, 30.0 μs), (7 kHz, 60.0 μs), (10 kHz, 40.0 μs), and (10 kHz, 20.0 μs).

In summary, one or more statistically-significant regions 100 can be defined for the optimal pulse width and frequency data taken for the patients in the study to arrive at combinations of pulse width and frequency that reduce pain without the side effect of paresthesia within the frequency range of 1 kHz to 10 kHz, and different statistical measures of error can be used to so define the one or more regions.

FIGS. 12A-12D show the results of testing other patients with sub-perception stimulation therapy at frequencies at or below 1 kHz. Testing of the patients generally occurred after supra-perception sweep spot searching occurred to select appropriate electrodes (E), polarities (P) and relative amplitudes (X %) for each patient (see FIGS. 7A-7D), although again the sub-perception electrodes used could vary from those used during the supra-perception sweet spot search (e.g., using MICC). Patients were tested with sub-perception stimulation using symmetric biphasic bipoles, although the form of pulses used during sub-perception therapy could vary.

Figure 12A:
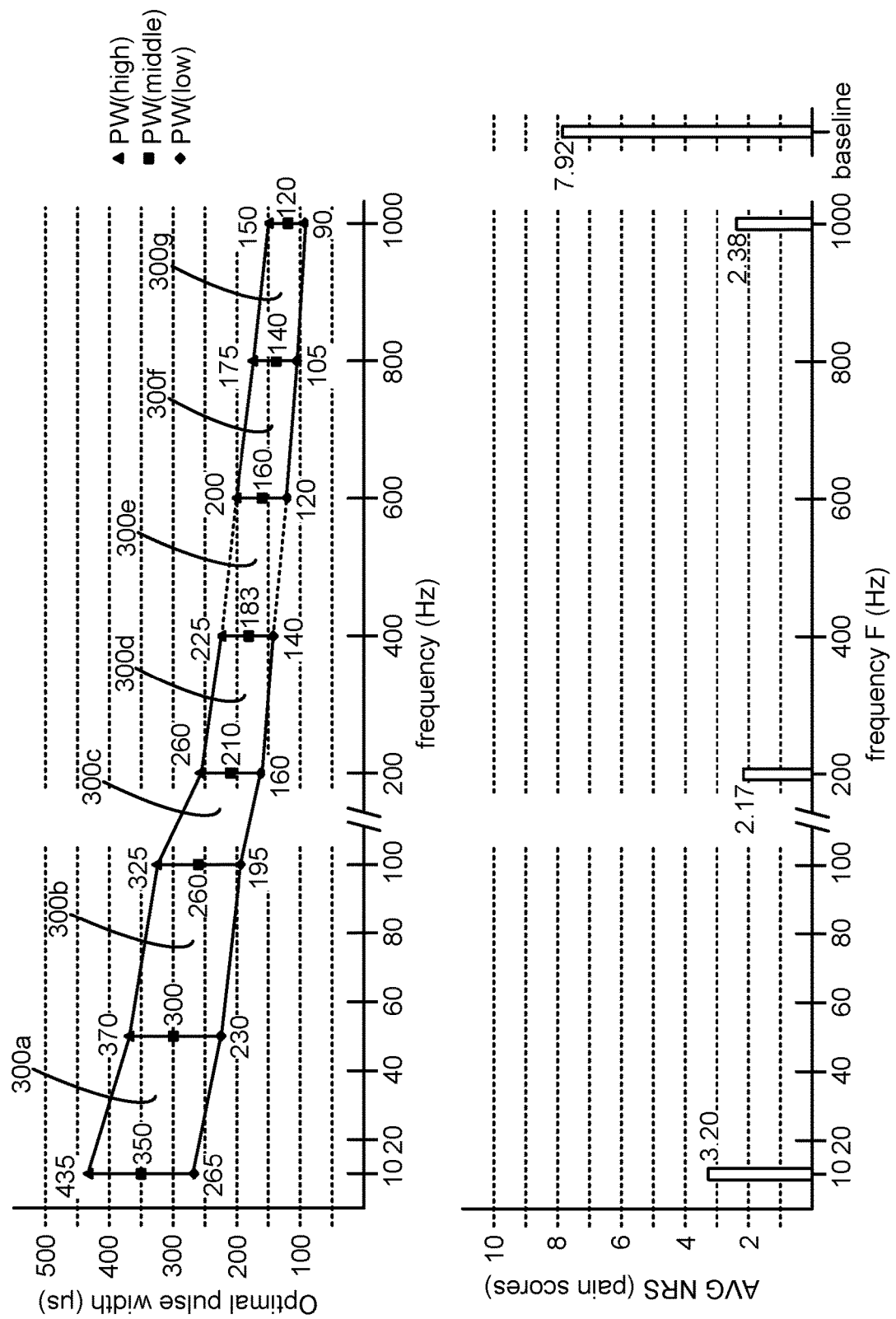
FIG. 12A shows results of patients tested with sub-perception therapy at frequencies at or below 1 kHz, and shows optimal pulse width ranges determined at tested frequencies, and optimal pulse width v. frequency regions for sub-perception therapy.

FIG. 12A shows the relationship between frequency and pulse width at which effective sub-perception therapy was reported by patients for frequencies of 1 kHz and below. Note that the same patient selection and testing criteria described earlier (FIG. 9) can be used when evaluating frequencies at or below 1 kHz, with the frequencies adjusted as appropriate.

As can be seen, at each frequency tested, the optimal pulse width again fell within a range. For example, at 800 Hz, patients reported good results when the pulse width fell within a range of 105-175 microseconds. The upper end of the pulse width range at each frequency is denoted PW(high), while the lower end of the pulse width range at each frequency is denoted PW(low). PW(middle) denotes the middle (e.g., average) of the PW(high) and PW(low) at each frequency. At each of the tested frequencies the amplitude of the current provided (A) was titrated down to sub-perception levels, such that the patient could not feel paresthesia. Typically, the current was titrated to 80% of the threshold at which paresthesia could be sensed. Because each patient's anatomy is unique, the sub-perception amplitude A could vary from patient to patient. The pulse width data depicted comprises the pulse width of only the first phase of the stimulation pulses.

Table 1 below expresses the optimal pulse width versus frequency data of FIG. 12A in tabular form for frequencies at or below 1 kHz, with the pulse widths expressed in microseconds:

TABLE 1

| Frequency (Hz) | PW(low) (μs) | PW(middle) (μs) | PW(high) (μs) |
|---|---|---|---|
| 1000 | 90 | 120 | 150 |
| 800 | 105 | 140 | 175 |
| 600 | 120 | 160 | 200 |
| 400 | 140 | 183 | 225 |
| 200 | 160 | 210 | 260 |
| 100 | 195 | 260 | 325 |
| 50 | 230 | 300 | 370 |
| 10 | 265 | 350 | 435 |

As with the analysis described earlier for frequencies in a range of 1 kHz to 10 kHz (FIGS. 10A-11C), the data may be broken down to define different regions 300i at which effective sub-perception therapy is realized below 1 kHz. For example, regions of effective sub-perception therapy may be linearly bounded between various frequencies and the high and low pulse widths that define effectiveness. For example, at 10 Hz, PW(low)=265 microseconds and PW(high)=435 microseconds. At 50 Hz, PW(low)=230 microseconds and PW(high)=370 microseconds. Therefore, a region 300a that provides good sub-perception therapy is defined by the linearly bounded region of points (10 Hz, 265 μs), (10 Hz, 435 μs), (50 Hz, 370 μs), and (50 Hz, 230 μs). Table 2 defines the points that linearly bind each of the regions 300a-300g shown in FIG. 12A:

TABLE 2

| region | Bounded by points (Hz, μs) |
|---|---|
| 300a | (10, 265), (10, 435), (50, 370), (50, 230) |
| 300b | (50, 230), (50, 370), (100, 325), (100, 195) |
| 300c | (100, 195), (100, 325), (200, 260), (200, 160) |
| 300d | (200, 160), (200, 260), (400, 225), (400, 140) |
| 300e | (400, 140), (400, 225), (600, 200), (600, 120) |
| 300f | (600, 120), (600, 200), (800, 175), (800, 105) |
| 300g | (800, 105), (800, 175), (1000, 150), (1000, 90) |

Regions of sub-perception therapeutic effectiveness at frequencies at or below 1 kHz may be defined in other statistically-significant ways, such as those described earlier for frequencies in the range of 1 kHz to 10 kHz (FIGS. 11A-11C). For example, regions 300i may be defined by reference to the pulse width at the middle of the ranges at each frequency, PW(middle). PW(middle) may comprise for example an average optimal pulse width reported by patients at each frequency, rather than as a strict middle of an effective range reported by those patients. PW(high) and PW(low) may then be determined as a statistical variance from the average PW(middle) at each frequency, and used to set the upper and lower bounds of effective sub-perception regions. For example, PW(high) may comprise average PW(middle) plus a standard deviation or standard error, or a multiples of such statistical measures; PW(low) may likewise comprise average PW(middle) minus a standard deviation or standard error, or a multiple of such statistical measures. PW(high) and PW(low) may also be determined from average PW(middle) in other ways. For example, PW(high) may comprise average PW(middle) plus a set percentage, while PW(low) may comprise PW(middle) minus a set percentage. In summary, one or more statistically-significant regions 300 can be defined for the optimal pulse width and frequency data at frequencies at or below 1 kHz that reduce pain using sub-perception stimulation without the side effect of paresthesia.

Also shown in FIG. 12A are average patient pain scores (NRS scores) reported by patients when optimal pulse widths are used for different frequencies at 1 kHz or below. Prior to receiving SCS therapy, patients initially reported pain scores with an average of 7.92. After SCS implantation, and using the sub-perception stimulation at optimal pulse widths with the ranges shown at each frequency, the patients' average pain scores dropped significantly. At 1 kHz, 200 Hz, and 10 Hz, patients reported average pain scores of 2.38, 2.17, and 3.20 respectively. Thus clinical significance with respect to pain relief is shown when the optimal pulse widths are used at or below 1 kHz with sub-perception therapy.

Figure 12B:
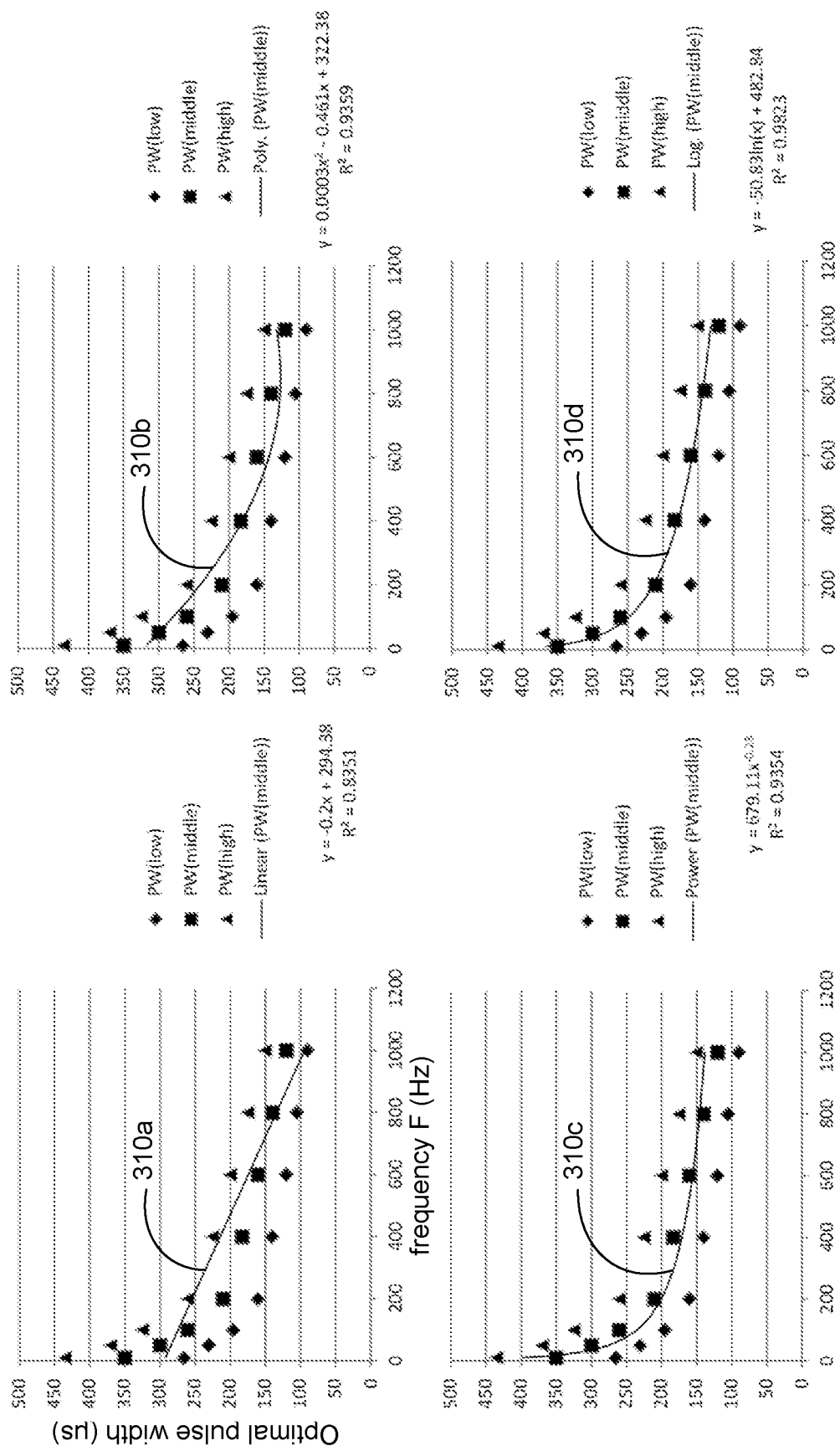
FIG. 12B shows various modelled relationships between average optimal pulse width and frequency at or below 1 kHz.

The optimal pulse width versus frequency data of FIG. 12A for frequencies at or below 1 kHz is analyzed in FIG. 12B from the perspective of the middle pulse width, PW(middle) at each frequency (F). As shown, the relationships 310a-310d follows statistically significant trends, as evidenced by the various regression models shown in FIG. 12B and summarized in Table 3 below:

TABLE 3

| Regression model | Relationship (PW(middle) in μs) | Correlation coefficient $R^2$ |
|---|---|---|
| Linear (310a) | PW(middle) = −0.2F + 294.4 | 0.835 |
| Polynomial (310b) | PW(middle) = $0.0002F^2$ − 0.461F + 332.38 | 0.936 |
| Power (310c) | PW(middle) = $679.1x^{-0.23}$ | 0.935 |
| Logarithmic (310d) | PW(middle) = −50.83ln(F) + 482.8 | 0.982 |

Other fitting methods could be used to establish other information relating frequency and pulse width at which stimulation pulses are formed to provide sub-perception pain relief without paresthesia.

Regression analysis can also be used to define statistically relevant regions such as 300a-300g where sub-perception therapy is effective at or below 1 kHz. For example, and although not shown in FIG. 12B, regression can be performed for PW(low) v. F to set a lower boundary of relevant regions 300i, and regression can be performed for PW(high) v. F to set an upper boundary of relevant regions 300i.

Figure 12C:
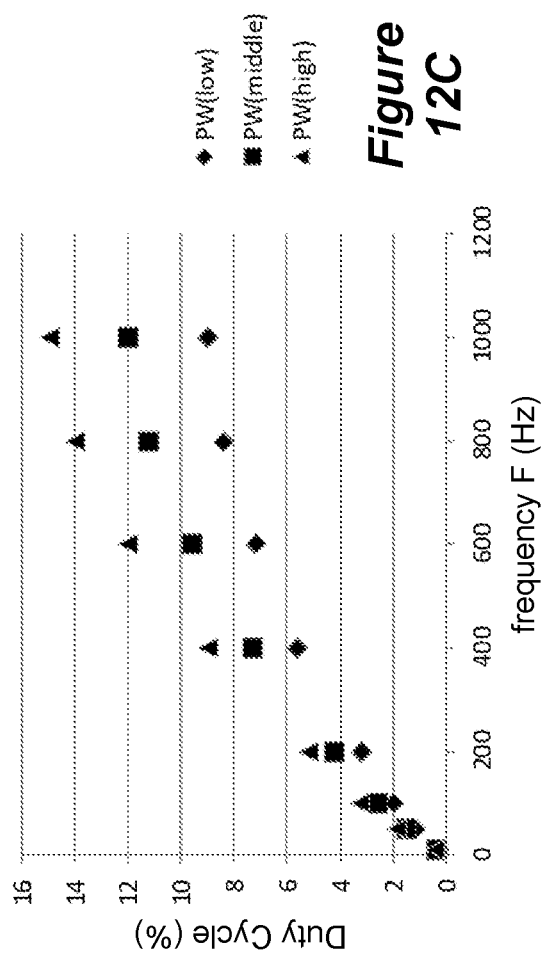
FIG. 12C shows the duty of cycle of the optimal pulse widths as a function of frequencies at or below 1 kHz.

Note that the relationship between optimal pulse width and frequency depicted in FIG. 12A is not simply an expected relationship between frequency and duty cycle (DC), as FIG. 12C shows. As was the case when the 1 kHz to 10 kHz frequency range was tested (FIG. 11A), the duty cycle of the optimal pulse widths is not constant at 1 kHz and below. Again, there is significance to the optimal pulse widths beyond a mere scaling of the frequency. Nonetheless, most of the pulse widths observed to be optimal at 1 kHz and below are greater than 100 microseconds. Such pulse widths are not even possible at higher frequencies. For example, at 10 kHz, both pulse phases have to fit within a 100 us period, so PW longer than 100 are not even possible.

Figure 12D:
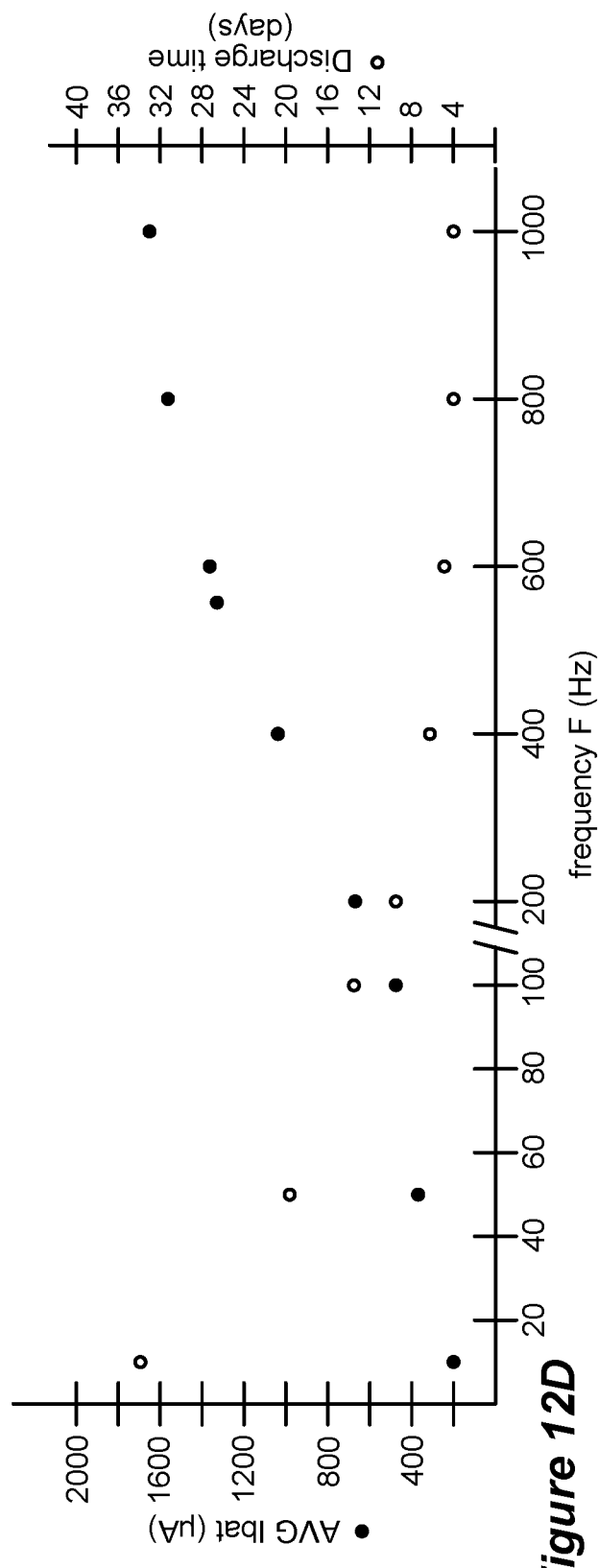
FIG. 12D shows the average battery current and battery discharge time at the optimal pulse widths as a function of frequencies at or below 1 kHz.

FIG. 12D shows further benefits achieved in using sub-perception at frequencies of 1 kHz and below, namely reduced power consumption. Two sets of data are graphed. The first data set comprises the average current drawn by the battery in the patients' IPG or ETS (AVG Ibat) at each frequency using the optimal pulse width for that patient (FIG. 12A) and the current amplitude A necessary to achieve sub-perception stimulation for that patient (again, this amplitude can vary for each of the patients). At 1 kHz, this average battery current is about 1700 microamps. However, as the frequency is reduced, this average battery current drops, to about 200 microamps at 10 Hz. The second data set looks at power consumption from a different vantage point, namely the number of days that an IPG or ETS with a fully-charged rechargeable battery can operate before recharge is required ("discharge time"). As would be expected based on the average battery current data, the discharge time is lower at higher frequencies when the average battery current is higher (e.g., about 3.9 days at 1 kHz, depending on various charging parameters and settings), and is higher at lower frequencies when the average battery current is lower (e.g., about 34 days at 10 Hz, depending on various charging parameters and settings). This is significant: not only can effective sub-perception therapy be provided at 1 kHz and below when optimal pulse widths are used; power consumptions is greatly lowered, which places less stress on the IPG or ETS, and allows it to operate from longer periods of time. As noted above, excessive power consumption is a significant problem when sub-perception therapy is traditionally used at higher frequencies. Note that the data of FIG. 12D could also be analyzed in terms of mean charge-per-second (MSC), as described earlier for the 1 kHz to 10 kHz data (FIG. 10B).

Once determined, the information 350 relating frequency and pulse width for optimal sub-perception therapy without paresthesia can be stored in an external device used to program the IPG 10 or ETS 40, such as the clinician programmer 50 or external controller 45 described earlier. This is shown in FIG. 13, in which the control circuitry 70 or 48 of the clinician programmer or external controller is associated with region information 100i or relationship information 98i for frequencies in the 1 kHz to 10 kHz range, and region information 300i or relationship information 310i for frequencies at or below 1 kHz. Such information can be stored in memory within or associated with the control circuitry. Storing of this information with the external device is useful to assisting the clinician with sub-perception optimization, as described further below. Alternatively, and although not shown, the information relating frequency and pulse width can be stored in the IPG 10 or ETS 40, thus allowing the IPG or ETS to optimize itself without clinician or patient input.

Information 350 can be incorporated into a fitting module. For example, fitting module 350 could operate as a software module within clinician programmer software 66, and may perhaps be implemented as an option selectable within the advanced 88 or mode 90 menu options selectable in the clinician programmer GUI 64 (FIG. 6). Fitting module 350 could also operate in the control circuitry of the IPG 10 or ETS 40.

The fitting module 350 can be used to optimize pulse width when frequency is known, or vice versa. As shown at the top of FIG. 13, the clinician or patient can enter a frequency F into the clinician programmer 50 or external controller 45. This frequency F is passed to the fitting module 350 to determine a pulse width PW for the patient, which is statistically likely to provide suitable pain relief without paresthesia. Frequency F could for example be input to the relationships 98*i* or 310*i* to determine the pulse width PW. Or, the frequency could be compared to the relevant region 100*i* or 300*i* within which the frequency falls. Once the correct region 100*i* or 300*i* is determined, F can be compared to the data in regions to determine a pulse width PW, which may perhaps be a pulse width between the PW+X and PW−X boundaries at the given frequency, as described earlier. Other stimulation parameters, such as amplitude A, active electrodes E, their relative percentage X %, and electrode polarity P can be determined in other manners, such as those described below, to arrive at a complete stimulation program (SP) for the patient. Based on the data from FIG. 10B, an amplitude near 3.0 mA might be a logical starting point, as this amplitude was show to be preferred by patients in the 1 kHz to 10 kHz range. However, other initial starting amplitudes may be chosen as well, which amplitudes for sub-perception therapy may be dependent on frequency. The bottom of FIG. 13 shows use of the fitting module 350 in reverse—that is to pick a frequency given a pulse width. Note that in the algorithms that follow or even when used outside of any algorithm, in one example, the system can allow the user to associate the frequency and pulse width such that when the frequency or pulse width is changed, the other of the pulse width or frequency is automatically changed to correspond to an optimal setting. In some embodiments, associating the frequency and pulse width in this manner can comprise a selectable feature (e.g., in GUI 64) useable when sub-perception programming is desired, and associating the frequency and pulse width can be unselected or unselectable for use with other stimulation modes.

Figure 14:
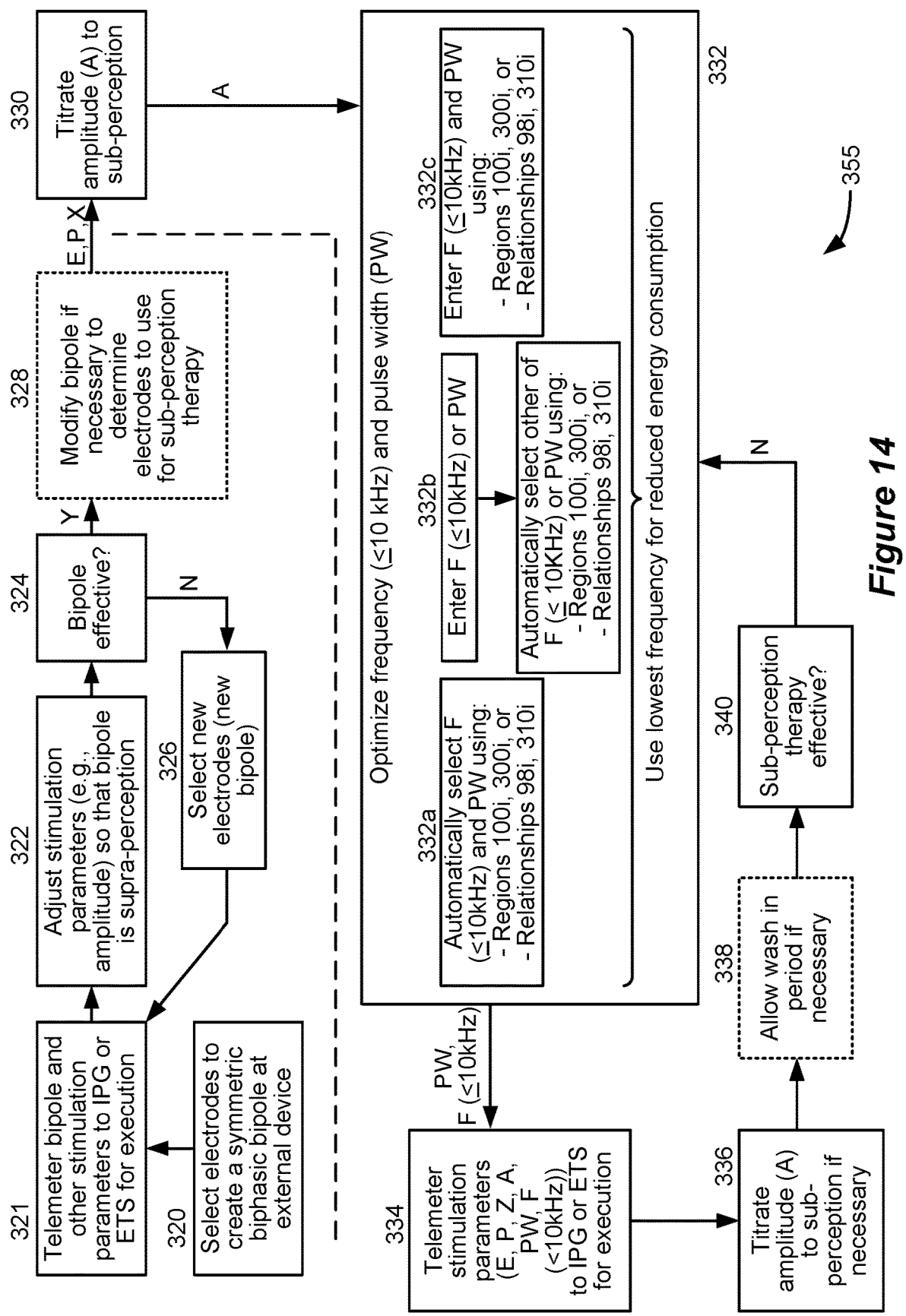
FIG. 14 shows an algorithm used for supra-perception sweet spot searching followed by sub-perception therapy, and possible optimization of the sub-perception therapy using the fitting module.

FIG. 14 shows an algorithm 355 that can be used to provide sub-perception therapy to an SCS patient at frequencies of 10 kHz or lower, and summarizes some of the steps already discussed above. Steps 320-328 describe the supra-perception sweep spot search. A user (e.g., clinician) selects electrodes to create a bipole for the patient (320), for example, by using the GUI of the clinician programmer. This bipole is preferably a symmetric biphasic bipole and may comprise a virtual bipole, as described earlier.

This bipole is telemetered along with other simulation parameters to the IPG or ETS for execution (321). Such other stimulation parameters can also be selected in the clinician programmer using the GUI. As a default, the frequency F can equal 90 Hz and the pulse width (PW) can equal 200 microseconds, although this is not strictly necessary and these values can be modified. At this point, if the bipole provided by the IPG or ETS is not supra-perception, i.e., if paresthesia is not felt by the patient, the amplitude A or other stimulation parameters can be adjusted to make it so (322). The bipole's effectiveness is then gauged by the patient (324) to see how well the bipole is covering the patient's pain site. NRS or other score rating systems can be used to judge effectiveness.

If the bipole is not effective, or if it is still desired to search, a new bipole can be tried (326). That is new electrodes can be selected preferably in manner which moves the bipole to a new location, along a path 296 as described earlier with reference to FIGS. 7A-7D. This new bipole can then again be telemetered to the IPG or ETS (321) and adjustments made if necessary to render the bipole supra-perceptive (322). If the bipole is effective, or if the searching is done and a most effective bipole has been located, that bipole may optionally be modified (328) prior to sub-perception therapy. Such modification as described above can involve selecting other electrodes proximate to the selected bipole's electrodes to modify the field shape in the tissue to perhaps better cover the patient's pain. As such, the modification of step 328 may change the bipole used during the search to a virtual bipole, or a tripole, etc.

Modification of other stimulation parameters can also occur at this point. For example, the frequency and pulse width can also be modified. In one example, a working pulse width can be chosen which provides good, comfortable paresthesia coverage (>80%). This can occur by using a frequency of 200 Hz for example, and starting with a pulse width of 120 microseconds for example. The pulse width can be increased at this frequency until good paresthesia coverage is noted. An amplitude in the range of 4 to 9 mA may be used for example.

At this point, the electrodes chosen for stimulation (E), their polarities (P), and the fraction of current they will receive (X %) (and possible a working pulse width) are known and will be used to provide sub-perception therapy. To ensure that sub-perception therapy is provided, the amplitude A of the stimulation is titrated downward to a sub-perception, paresthesia free level (330), and telemetered to the IPG or ETS. As described above, the amplitude A may be set below an amplitude threshold (e.g., 80% of the threshold) at which the patient can just start to feel paresthesia.

At this point, it can be useful to optimize the frequency and pulse width of the sub-perception therapy that is being provided to the patient (332). While the frequency (F) and pulse width (PW) used during sweet spot searching can be used for sub-perception therapy, benefit is had by additionally adjusting these parameters to optimal values in accordance with the regions 100*i* or relationships 98*i* established at frequencies in the 1 kHz to 10 kHz range, or the regions 300*i* or relationships 310*i* established at frequencies at or below 1 kHz. Such optimization may use the fitting module 350 of FIG. 13, and can occur in different ways, and a few means of optimization 332*a*-332*c* are shown in FIG. 14. Option 332*a* for instance allows the software in either the clinician programmer or the IPG or ETS to automatically select both a frequency (≤10 kHz) and pulse width using the region or relationship data correlating frequency to pulse width. Option 332*a* might use the working pulse width determined earlier (328), and choose a frequency using the regions or relationships. Option 332*b* by contrast allows the user (clinician) to specify (using the GUI of the clinician program) either the frequency (≤10 kHz) or the pulse width. The software can then select an appropriate value for the other parameter (pulse width or frequency (≤10 kHz), again using regions or the relationships. Again, this option might use the working pulse width determined earlier to select an appropriate frequency. Option 332*c* allows the user to enter both the frequency (≤10 kHz) and the pulse width PW, but in a manner that is constrained by the regions or the relationships. Again, this option may allow the use to enter the working pulse width and a frequency that is appropriate for that working frequency, depending on the regions or relationships. The GUI 64 of the clinician programmer might in this example not accept inputs for F and PW that do not fall within the regions or along the relationships because such values would not provide optimal sub-perception therapy.

Frequency or pulse width optimization can occur other ways that more effectively search the desired portion of the parameter space. For example, a gradient descent, binary search, simplex method, genetic algorithm, etc. can be used for the search. A machine learning algorithm that has trained using data from patients could be considered.

Preferably, when optimizing the frequency (≤10 kHz) and pulse width at step 332, these parameters are selected in a manner that reduces power consumption. In this regard, it is preferable that the lowest frequency be chosen, as this will reduce mean charge per second (MCS), reduce the average current drawn from the battery in the IPG or ETS, and thus increase the discharge time, as discussed earlier with respect to FIGS. 10B and 12D. Lowering the pulse width if possible will also reduce battery draw and increase the discharge time.

At this point all relevant stimulation parameters (E, P, X, I, PW, and F (≤10 kHz)) are determined and can be sent from the clinician programmer to the IPG or ETS for execution (334) to provide sub-perception stimulation therapy for the patient. It is possible that adjustment of the optimal pulse width and frequency (≤10 kHz) (332) may cause these stimulation parameters to provide paresthesia. Therefore, the amplitude of the current A can once again be titrated downward to sub-perception levels if necessary (336). If necessary, the prescribed sub-perception therapy can be allowed a period of time to wash in (338), although as mentioned earlier this may not be necessary as the supra-perception sweet spot search (320-328) has selected electrodes for situation that well recruit the patient's pain site.

If sub-perception therapy is not effective, or could use adjustment, the algorithm can return to step 332 to selection of a new frequency (≤10 kHz) and/or pulse width in accordance with the regions or relationships defined earlier.

It should be noted that not all parts of steps of the algorithm of FIG. 14 need be performed in an actual implementation. For example, if effective electrodes are already known (i.e., E, P, X), then the algorithm may begin with sub-perception optimization using the information relating frequency and pulse width.

Figure 15:
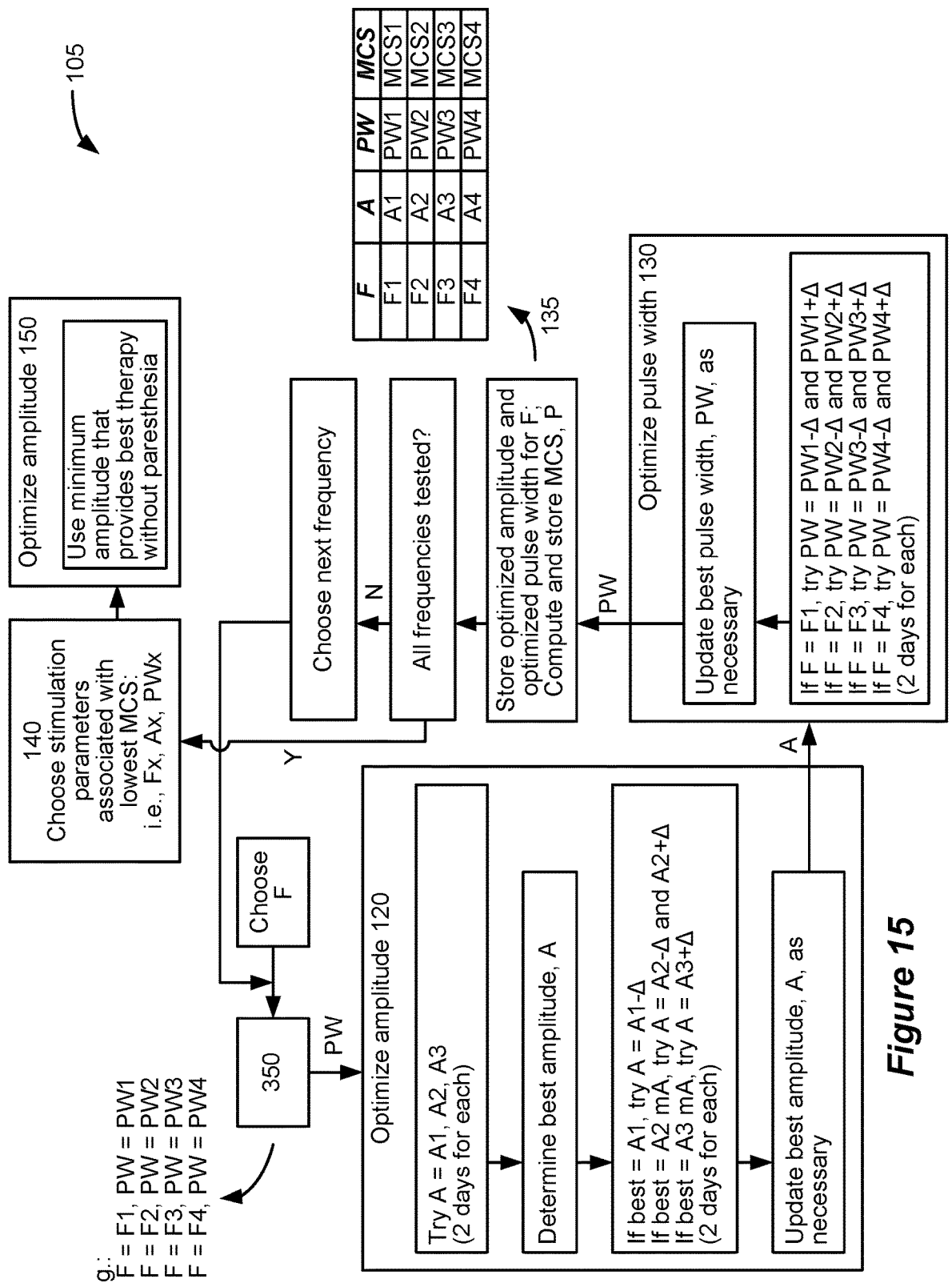
FIG. 15 shows an alternative algorithm for optimization of the sub-perception therapy using the fitting module.

FIG. 15 shows another manner in which fitting module 350 (FIG. 13) can be used to determine optimal sub-perception stimulation for a patient at frequencies of 10 kHz or less. In FIG. 15, the fitting module 350 is again incorporated within or used by an algorithm 105, which again can be executed on the external device's control circuitry as part of its software, or in the IPG 10. In the algorithm 105, the fitting module 350 is used to pick initial pulse widths given a particular frequency. Algorithm 105 is however more comprehensive as it will test and optimize amplitudes and further optimize pulse widths at different frequencies. As explained further below, algorithm 105 further optionally assists in picking optimized stimulation parameters that will result in the lowest power requirements that are most considerate of the IPG's battery 14. Some steps illustrated in FIG. 15 for algorithm 105 are optional, and other steps could be added as well. It is assumed that a sweet spot search for a patient being tested by algorithm 105 has already occurred, and that electrodes (E, P, X) have already been chosen and preferably will remain constant throughout operation of the algorithm. However, this is not strictly required, as these electrode parameters can also be modified, as described above.

Algorithm 105 begins by picking an initial frequency (e.g., F1) within the range of interest (e.g., ≤10 kHz). Algorithm 105 then passes this frequency to the fitting module 350, which uses the relationships and/or regions determined earlier to pick an initial pulse width PW1. For simplicity, fitting module 350 is illustrated in FIG. 15 as a simple look up table of pulse width versus frequency, which can comprise another form of information relating frequency and pulse width at which stimulation pulses are formed to provide pain relief without paresthesia. Selection of a pulse width using fitting module 350 could be more sophisticated, as described earlier.

After selection of a pulse width for the given frequency, stimulation amplitude A is optimized (120). Here, a number of amplitudes are chosen and applied to the patient. In this example, the chosen amplitudes are preferably determined using an optimal amplitude A determined at each frequency (see, e.g., FIG. 10B). Thus, amplitudes at A=A2, below (A1), and above (A3) are tried by the patient for a period (e.g., two days each). A best of these are picked by the patient. At this point, further adjustments to amplitude can be tried to try and hone in on an optimal amplitude for the patient. For example, if A2 is preferred, amplitudes slightly above (A2+Δ) and below (A2-Δ) below this can be tried for a period. If a lower value of A1 was preferred, an even lower amplitude (A1-Δ) can be tried. If a higher value of A3 was preferred, an even higher amplitude (A3+Δ) can be tried. Ultimately, such iterative testing of amplitude arrives at an effective amplitude for the patient that does not induce paresthesia.

Next, the pulse width can be optimized for the patient (130). As with amplitude, this can occur by slightly lowering or increasing the pulse width chosen earlier (350). For example, at a frequency of F1 and an initial pulse width of PW1, the pulse width may be lowered (PW1-Δ) and increased (PW1+Δ) to see if such settings are preferred by the patient. Further iterative adjustment of amplitude and pulse width may occur at this point, although this is not illustrated.

In short, at a given frequency, an initial pulse width (350) (and preferably also an initial amplitude (120)) are chosen for a patient, because it would be expected that these values would likely provide effective and paresthesia-free pain relief. Nonetheless, because each patient is different, the amplitude (120) and pulse width (130) are also adjusted from the initial values for each patient.

Thereafter, the optimal stimulation parameters determined for the patient at the frequency being tested are stored in the software (135). Optionally, a mean charge per second (MCS) indicative of the neural dose the patient receives, or other information indicative of power draw (e.g., average Ibat, discharge time) is also calculated and also stored. If still further frequencies in the range of interest have not been tested (e.g., F2), they are then tested as just described.

Once one or more frequencies have been tested, stimulation parameters can be chosen for the patient (140), using the optimal stimulation parameters stored earlier for the patient at each frequency (135). Because the stimulation parameters at each frequency are suitable for the patient, the stimulation parameters chosen can comprise that which results in the lowest power draw (e.g., the lowest) MCS. This is desired, because these stimulation parameters will be easiest on the IPG's battery. It might be expected that the stimulation parameters determined by algorithm 105 to have the lowest MCS would comprise those taken at the lowest frequency. However, every patient is different, and therefore this might not be the case. Once the stimulation parameters have been chosen, further amplitude optimization can be undertaken (150), with the goal of choosing a minimum amplitude that provides sub-perception pain relief without paresthesia.

It should be noted the use of the disclosed technique should not necessarily be limited to the specific frequencies tested. Other data suggests applicability of the disclosed technique to provide pain relief without paresthesia at frequencies as low as 2 Hz.

Various aspects of the disclosed techniques, including processes implementable in the IPG or ETS, or in external devices such as the clinician programmer or external controller to render and operate the GUI 64, can be formulated and stored as instructions in a computer-readable media associated with such devices, such as in a magnetic, optical, or solid state memory. The computer-readable media with such stored instructions may also comprise a device readable by the clinician programmer or external controller, such as in a memory stick or a removable disk, and may reside elsewhere. For example, the computer-readable media may be associated with a server or any other computer device, thus allowing instructions to be downloaded to the clinician programmer system or external controller or to the IPG or ETS, via the Internet for example.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for programming stimulation in a spinal cord stimulator (SCS) system, comprising:
   selecting a first frequency and a first pulse width for first stimulation pulses to be produced by the SCS device using a mathematical function relating frequencies and pulse widths at which stimulation pulses are formed to provide pain relief without paresthesia; and
   programming stimulation circuitry in the SCS system to generate first stimulation pulses with the selected first frequency and the selected first pulse width at at least one of a plurality of electrodes.

2. The method of claim 1, wherein the system comprises an implantable stimulator device.

3. The method of claim 1, wherein the stimulation pulses form a bipole in the patient's tissue.

4. The method of claim 1, wherein the SCS device further comprises control circuitry, wherein the mathematical function is stored in the control circuitry.

5. The method of claim 4, wherein the first frequency is provided to the control circuitry and the first pulse width is determined using the mathematical function, or wherein the first pulse width is provided to the control circuitry and the first frequency is determined using the mathematical function.

6. The method of claim 1, wherein the stimulation circuitry is programmed by an external device comprising control circuitry, wherein the mathematical function is stored in the control circuitry.

7. The method of claim 6, wherein the first frequency and the first pulse width are selected in the external device.

8. The method of claim 7, wherein programming the stimulation circuitry in the SCS device comprises wirelessly transmitting the selected first frequency and the selected first pulse width to the SCS device from the external device.

9. The method of claim 1, wherein each of the stimulation pulses comprises a biphasic pulse having a first phase of a first polarity and a second phase of a second polarity opposite the first polarity, wherein the first and second phases are actively driven by the stimulation circuitry in the SCS device to generate the stimulation pulses.

10. The method of claim 9, wherein each of the stimulation pulses comprises a symmetric biphasic pulse, wherein a duration of the first phase is equal to a duration of the second phase, and wherein an amplitude of the first phase is equal but of opposite polarity to an amplitude of the second phase.

11. The method of claim 1, wherein the selected first frequency is lower than or equal to 10 kHz.

12. The method of claim 1, wherein the mathematical function relating frequencies and pulse widths does not comprise a duty cycle that is constant in a range of 10 Hz through 1 kHz.

13. The method of claim 1, further comprising programming the stimulation circuitry to steer the stimulation pulses away from the at least one of the plurality of electrode and to one or more different of the plurality of electrodes to adjust a location at which the stimulation pulses are applied to the patient.

14. The method of claim 13, further comprising programming the stimulation circuitry to adjust an amplitude of the stimulation pulses based on the adjusted location at which the stimulation pulses are applied to the patient.

15. The method of claim 1, wherein the first frequency and the first pulse width comprise two of a set of stimulation parameters used to generate the stimulation pulses, and further comprising programming the stimulation circuitry to adjust at least one of the stimulation parameters in response to a change in position or activity of the patient.

16. The method of claim 1, wherein the SCS device is programmed during a programming session, and wherein the stimulation pulses wash in for a period of one hour or less during the programming session to provide pain relief to the patient without paresthesia.

17. The method of claim 1, wherein the first frequency and the first pulse width are selected using the mathematical function to require a lowest amount of power for the stimulation pulses.

18. The method of claim 1, wherein the mathematical function is pre-determined.

19. The method of claim 1, wherein the selected first frequency and the selected pulse width are on or within one or more linearly-bounded regions defined by points:
   (i) (10 Hz, 265 µs), (10 Hz, 435 µs), (50 Hz, 370 µs), and (50 Hz, 230 µs); or
   (ii) (50 Hz, 230 µs), (50 Hz, 370 µs), (100 Hz, 325 µs), and (100 Hz, 195 µs); or
   (iii) (100 Hz, 195 µs), (100 Hz, 325 µs), (200 Hz, 260 µs), and (200 Hz, 160 µs); or
   (iv) (200 Hz, 160 µs), (200 Hz, 260 µs), (400 Hz, 225 µs), and (400 Hz, 140 µs); or
   (v) (400 Hz, 140 µs), (400 Hz, 225 µs), (600 Hz, 200 µs), and (600 Hz, 120 µs); or
   (vi) (600 Hz, 120 µs), (600 Hz, 200 µs), (800 Hz, 175 µs), and (800 Hz, 105 µs); or
   (vii) (800 Hz, 105 µs), (800 Hz, 175 µs), (1 kHz, 150 µs), and (1 kHz, 90 µs); or
   (vii) (1 kHz, 98.3 µs), (1 kHz, 109 µs), (4 kHz, 71.4 µs), and (4 kHz, 64.6 µs); or (ix) (4 kHz, 71.4 µs), (4 kHz, 64.6 µs), (7 kHz, 44.2 µs), and (7 kHz, 48.8 µs); or (x) (7 kHz, 44.2 µs), (7 kHz, 48.8 µs), (10 kHz, 29.9 µs), and (10 kHz, 27.1 µs).

* * * * *